(12) United States Patent
Frydman et al.

(10) Patent No.: US 11,904,125 B2
(45) Date of Patent: Feb. 20, 2024

(54) MANUKA HONEY MICRONEEDLE

(71) Applicant: Massachusetts Institute of Technology, Cambridge, MA (US)

(72) Inventors: Galit Frydman, Boston, MA (US); David Olaleye, Indianapolis, IN (US); Illina Yang, Sunnyvale, CA (US); Damodaran Annamalai, Norwood, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 701 days.

(21) Appl. No.: 16/893,922

(22) Filed: Jun. 5, 2020

(65) Prior Publication Data
US 2020/0384254 A1    Dec. 10, 2020

Related U.S. Application Data

(60) Provisional application No. 62/858,638, filed on Jun. 7, 2019.

(51) Int. Cl.
| | | |
|---|---|---|
| A61M 37/00 | (2006.01) | |
| A61P 17/02 | (2006.01) | |
| A61P 31/04 | (2006.01) | |
| A61K 35/644 | (2015.01) | |
| A61K 45/06 | (2006.01) | |

(52) U.S. Cl.
CPC ....... *A61M 37/0015* (2013.01); *A61K 35/644* (2013.01); *A61P 17/02* (2018.01); *A61P 31/04* (2018.01); *A61K 45/06* (2013.01); *A61M 2037/0023* (2013.01); *A61M 2037/0046* (2013.01); *A61M 2037/0053* (2013.01); *A61M 2207/00* (2013.01)

(58) Field of Classification Search
None
See application file for complete search history.

(56) References Cited

FOREIGN PATENT DOCUMENTS

| CN | 108714273 A | 10/2018 |
|---|---|---|
| WO | WO-2013/188884 A1 | 12/2013 |
| WO | WO-2020/247739 A1 | 12/2020 |

OTHER PUBLICATIONS

International Search Report and Written Opinion for International Application No. PCT/US2020/036308 dated Sep. 17, 2020.
Martin et al., "Low temperature fabrication of biodegradable sugar glass microneedles for transdermal drug delivery applications," Journal of Controlled Release, 158(1): 93-101 (2012).
Alvarez-Suarez et al., "The Composition and Biological Activity of Honey: A Focus on Manuka Honey," Foods, 3(3): 420-432 (2014).
Anderson., "Surgical site infections," Infectious Disease Clinics of North America, 25(1): 135-153 (2011).
Biesman et al., "Treatment of Atrophic Facial Acne Scars With Microneedling Followed by Polymethylmethacrylate-Collagen Gel Dermal Filler," Dermatologic Surgery, 45(12): 1570-1579 (2019).
Carter et al., "Therapeutic Manuka Honey: No Longer So Alternative," Frontiers in Microbiology, 7: Article 569 (2016).
Chen et al., "Chitosan Microneedle Patches for Sustained Transdermal Delivery of Macromolecules," Biomacromolecules, 13(12): 4022-4031 (2012).
Cooper et al., "Absence of bacterial resistance to medical-grade manuka honey," European Journal of Clinical Microbiology & Infectious Diseases, 29: 1237-1241 (2010).
Engemann et al., "Adverse Clinical and Economic Outcomes Attributable to Methicillin Resistance among Patients with *Staphylococcus aureus* Surgical Site Infection," Clinical Infectious Diseases, 36: 592-598 (2003).
Gamazo et al., "Understanding the basis of transcutaneous vaccine delivery," Therapeutic Delivery, 10(1): 63-80 (2019).
General and Plastic Surgery Panel of the Medical Device Advisory Committee on Classification of Devices: 2016.
Hilliard et al., "Preliminary investigation of honey-doped electrospun scaffolds to delay wound closure," Journal of Biomedical Materials Research Part B Applied Biomaterials, 107(8): 2620-2628 (2019).
Hixon et al., "Investigating Manuka Honey Antibacterial Properties When Incorporated into Cryogel, Hydrogel, and Electrospun Tissue Engineering Scaffolds," Gels, 5(2): E21 (2019).
Ibrahim et al., "Therapeutic effect of microneedling and autologous platelet rich plasma in the treatment of atrophic scars: A randomized study," Journal of Cosmetic Dermatology, 16(3): 388-399 (2017).
Janzowski et al., "5-Hydroxymethylfurfural: assessment of mutagenicity, DNA-damaging potential and reactivity towards cellular glutathione," Food and Chemical Toxicology, 38(9): 801-809 (2000).
Jenkins et al., "Manuka honey inhibits cell division in methicillin-resistant *Staphylococcus aureus*," Journal of Antimicrobial Chemotherapy, 66(11): 2536-2542 (2011).
Kwakman et al., "How honey kills bacteria," The FASEB Journal, 24(7): 2576-2582 (2010).
Liu et al., "Rifampin-manuka honey combinations are superior to other antibiotic-manuka honey combinations in eradicating *Staphylococcus aureus* biofilms," Frontiers in Microbiology, 8: 2653 (2018).
Maddocks et al., "Manuka honey inhibits the development of *Streptococcus pyogenes* biofilms and causes reduced expression of two fibronectin binding proteins," Microbiology, 158(Pt 3): 781-790 (2012).

(Continued)

*Primary Examiner* — Robert A Wax
*Assistant Examiner* — Quanglong N Truong
(74) *Attorney, Agent, or Firm* — Foley Hoag LLP; Alexander Akhiezer; Lawrence P. Tardibono

(57) ABSTRACT

A device, comprising a base, and a plurality of microneedles attached to the base, wherein the microneedles comprise dehydrated honey having water content of less than 5% by weight. The dehydrated honey can be a Manuka dehydrated honey. Also disclosed are methods of fabricating and using the disclosed device.

11 Claims, 14 Drawing Sheets

(56) References Cited

OTHER PUBLICATIONS

McKibben et al., "Guidance on Public Reporting of Healthcare-Associated Infections: Recommendations of the Healthcare Infection Control Practices Advisory Committee," American Journal of Infection Control, 34(3): 217-226 (2005).

Mechcatie., "FDA Clears Honey-Based Dressing," Caring for the Ages: (2007).

Minden-Birkenmaier et al., "Honey-based templates in wound healing and tissue engineering," Bioengineering, 5(2): E46 (2018).

National Nosocomial Infections Surveillance (NNIS) Report., American Journal of Infection Control 24(5): 380-388, Data Summary from Oct. 1986-Apr. 1996, Issued May 1996.

Negut et al., "Treatment strategies for infected wounds," Molecules, 23(9): E2392 (2018).

Neres Santos et al., "Physically cross-linked gels of PVA with natural polymers as matrices for Manuka honey release in wound-care applications," Materials, 12(4): E559 (2019).

Park et al., "Polymer microneedles for controlled-release drug delivery," Pharmaceutical Research, 23(5): 1008-1019 (2006).

Petti et al., "Postoperative Bacteremia Secondary to Surgical Site Infection," Clinical Infectious Diseases, 34(3): 305-308 (2002).

Ranzato et al., "Honey exposure stimulates wound repair of human dermal fibroblasts," Burns & Trauma, 1(1): 32-38 (2013).

Severin et al., "Genotoxic activities of the food contaminant 5-hydroxymethylfurfural using different in vitro bioassays," Toxicology Letters, 192(2): 189-194 (2010).

Singh et al., "Scar free healing mediated by the release of aloe vera and manuka honey from dextran bionanocomposite wound dressings," International Journal of Biological Macromolecules, 120(Part B): 1581-1590 (2018).

Wang et al., "Recent advances in the design of polymeric microneedles for transdermal drug delivery and biosensing," Lab on a Chip, 17(8): 1373-1387 (2017).

Fig. 4

| Honey stage | Sugar Content (%) | Temp. (°C) | Pressure (atm) | Temp. (°C) | Pressure (atm) | Temp. (°C) | Pressure (atm) |
|---|---|---|---|---|---|---|---|
| Thread | 80 | 110-115 | 1.00 | 25 | .023 | 45 | 0.41 |
| soft ball | 85 | 120 | 1.00 | 25 | 0.015 | 45 | 0.22 |
| hard ball | 92 | 120-130 | 1.00 | 25 | 0.011 | 45 | 0.21 |
| soft crack | 95 | 130-140 | 1.00 | 25 | 0.0085 | 45 | 0.19 |
| hard crack | 99 | >150 | 1.00 | 25 | 0.0023 | 45 | 0.16 |

Fig. 10

| Bacteria Dilutions[a] | Honey Conditions | | | | | | Control | Control |
|---|---|---|---|---|---|---|---|---|
| | Cooked | | Vacuum | | Raw | | TSB | Raw (50%) |
| | 10%[b] | 1%[b] | 10% | 1% | 10% | 1% | | |
| $10^{-1}$ | +/+/+[c] | + | +/+/- | + | + | + | + | - |
| $10^{-2}$ | +/+/+ | + | +/+/- | + | + | + | + | - |
| $10^{-3}$ | +/-/- | + | -/+/- | + | + | + | + | - |
| $10^{-4}$ | - | + | - | + | - | + | + | - |
| $10^{-5}$ | - | + | - | + | - | + | + | - |
| $10^{-6}$ | - | -/+/+ | - | + | - | + | + | - | a. Stock concentration of MRSA bacteria was about $8 \times 10^8$ CFU/mL. (OD 0.78)
b. Concentration of the honey diluted in TSB broth (%) calculated by weight of honey
c. + signifies presence of bacterial colonies, - signifies no bacterial growth noted; / is used when the replicates had different results, no / signifies all replicates yielded the same results Fig. 13
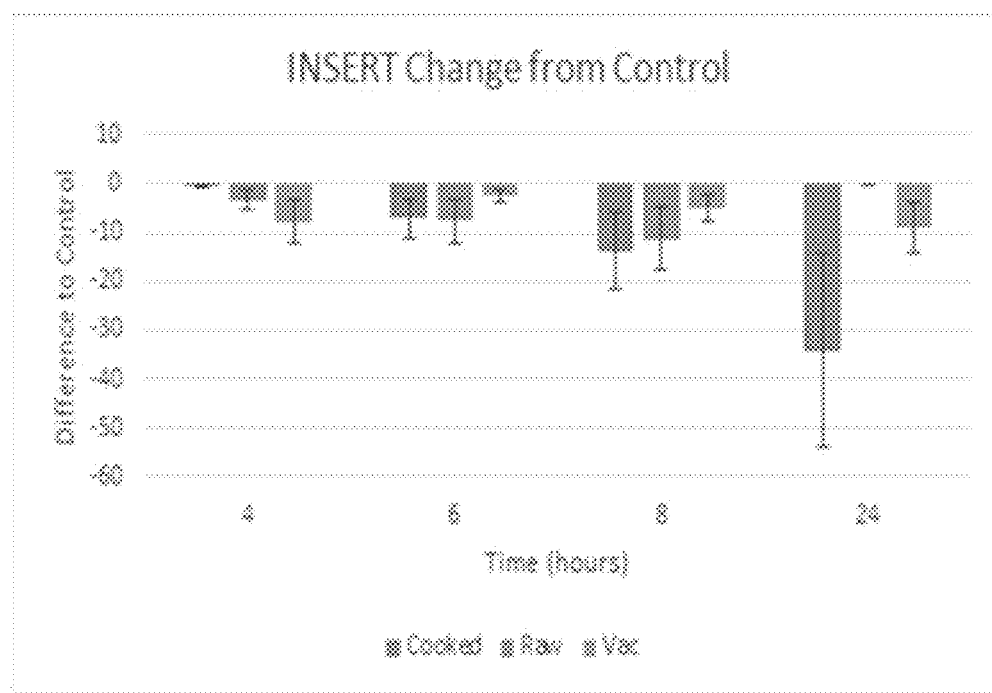
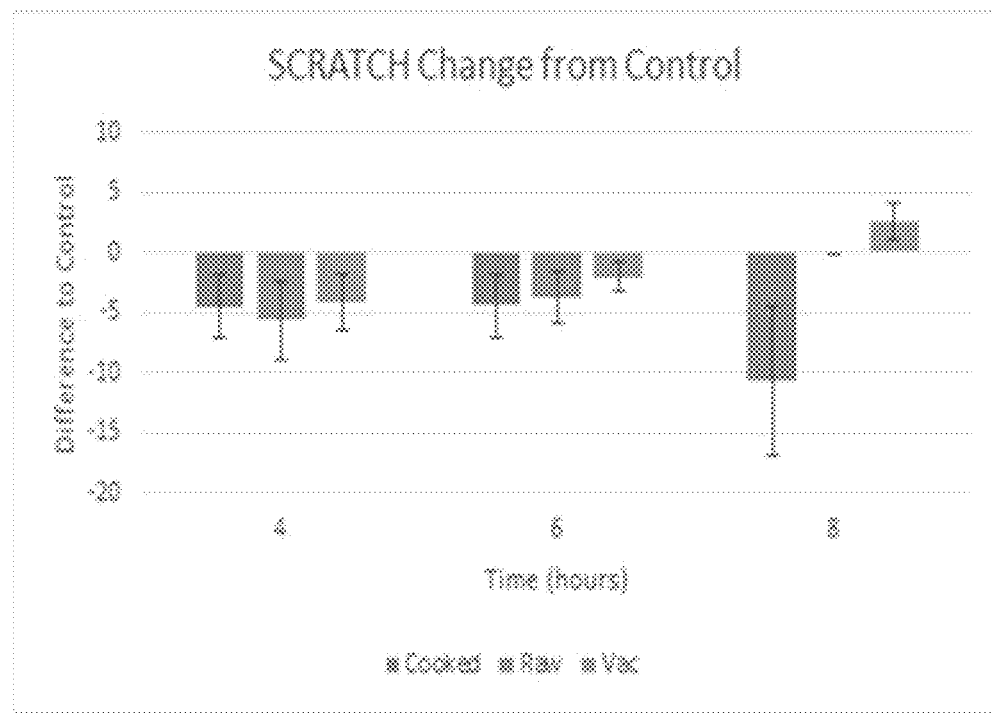

Fig. 14

Insert

| 4 hrs | Raw | Vacuum | Cooked |
|---|---|---|---|
| Control | 0.16 | 0.59 | 0.05 |
| Raw | | 0.50 | 0.62 |
| Vacuum | | | 0.80 |

| 6 hrs | Raw | Vacuum | Cooked |
|---|---|---|---|
| Control | 0.21 | 0.67 | 0.02 |
| Raw | | 0.26 | 0.72 |
| Vacuum | | | 0.42 |

| 8 hrs | Raw | Vacuum | Cooked |
|---|---|---|---|
| Control | 0.16 | 0.02 | 0.02 |
| Raw | | 0.88 | 0.54 |
| Vacuum | | | 0.05 |

| 24 hrs | Raw | Vacuum | Cooked |
|---|---|---|---|
| Control | 0.97 | 0.36 | 0.07 |
| Raw | | 0.19 | 0.08 |
| Vacuum | | | 0.05 |

Scratch

| 4 hrs | Raw | Vacuum | Cooked |
|---|---|---|---|
| Control | 0.133 | 0.57 | 0.35 |
| Raw | | 0.01 | 0.81 |
| Vacuum | | | 0.25 |

| 8 hrs | Raw | Vacuum | Cooked |
|---|---|---|---|
| Control | 0.49 | 0.53 | 0.35 |
| Raw | | 0.87 | 0.43 |
| Vacuum | | | 0.04 |

| 24 hrs | Raw | Vacuum | Cooked |
|---|---|---|---|
| Control | 0.14 | 0.75 | 0.05 |
| Raw | | 0.07 | 0.12 |
| Vacuum | | | 0.01 |

Fig. 15
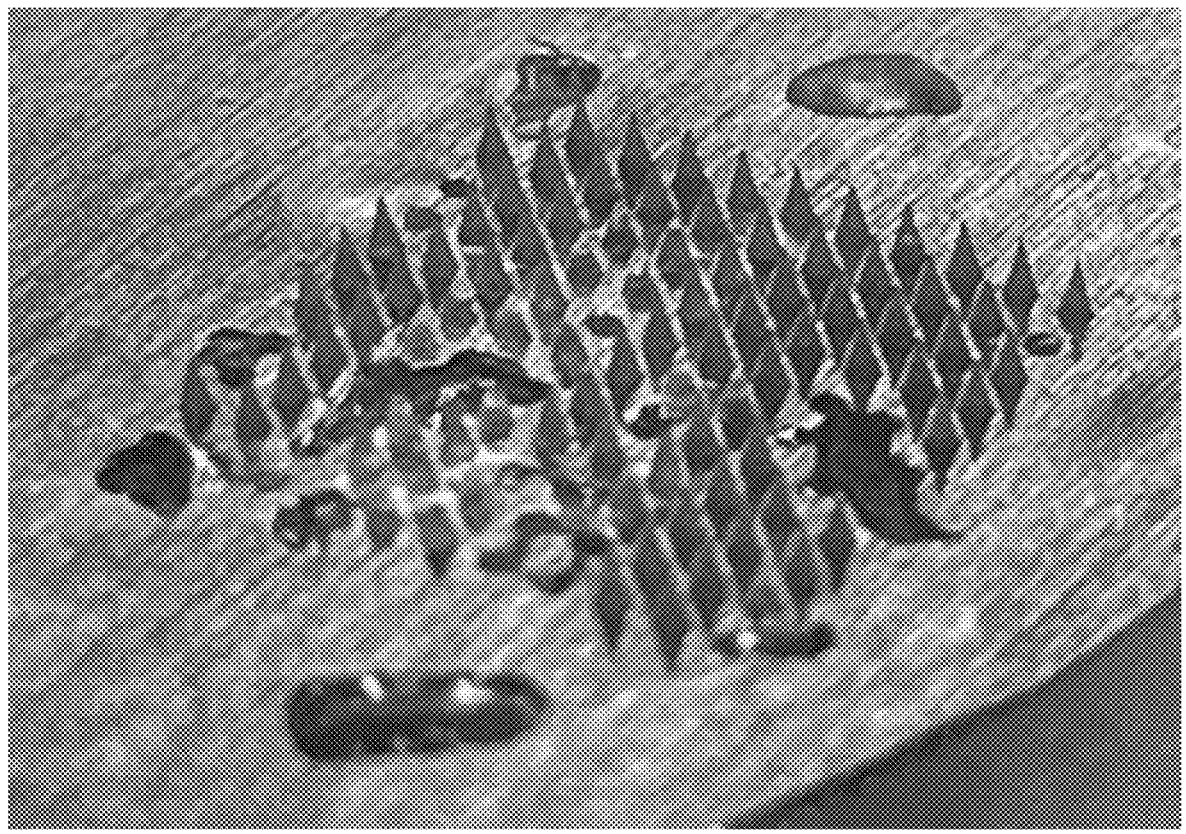
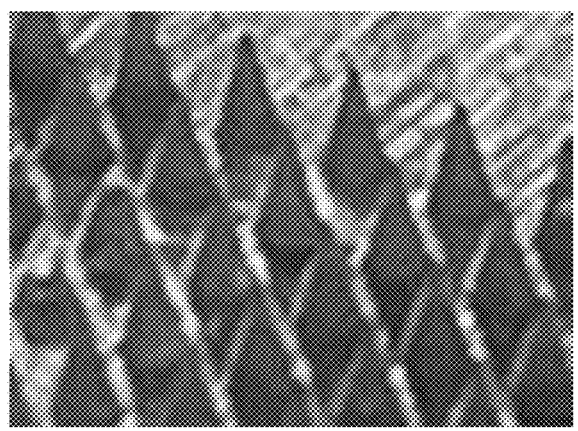

MANUKA HONEY MICRONEEDLE

RELATED APPLICATION(S)

This application claims the benefit of U.S. Provisional Application No. 62/858,638, filed on Jun. 7, 2019. The entire teachings of the above application are incorporated herein by reference.

GOVERNMENT SUPPORT

This invention was made with Government support under Grant Nos. P41 EB002503 and P30 ES002109 awarded by the National Institutes of Health (NIH). The Government has certain rights in the invention.

BACKGROUND OF THE INVENTION

Methicillin-resistant *Staphylococcus aureus* (MRSA) is the most common cause of Surgical site infections (SSIs). SSIs have historically been associated with increased morbidity and mortality, but remain an issue in modern day healthcare. As of 2017, the Centers for Disease Control and Prevention (CDC) estimated that SSIs occurred in at least 1.9% of all surgical patients; however, this number is most likely not representative of the total number of SSI cases since about 50% of SSIs occur after hospital discharge (Anderson, D. J. (2011) Surgical Site Infections. *Infectious Disease Clinics of North America*; McKibben, L., Horan T., Tokars J. I., Fowler, G., Cardo, D. M., Pearson, M. L., Brennan, P. J. & Healthcare Infection Control Practices Advisory Committee. (2005). *Infection Control and Hospital Epidemiology*). MRSA is the most common cause of SSIs leading in an increased morbidity in patients and increased hospital charges (Petty, C. A., Sanders, L. L., Trivette, S. L., Briggs J. & Sexton D. J. (2002). Postoperative Bacteremia Secondary to Surgical Site Infection. *Clinical Infectious Diseases*; National Nosocomial Infections Surveillance (NNIS) Report, Data Summary from October 1986-April 1996, Issued May 1996. A report from the National Nosocomial Infections Surveillance (NNIS) System). In a study evaluating the 90-day mortality rate in patients with SSI, it was discovered that patients with a methicillin-resistant *Staphylococcus aureus* (MRSA) SSI had a 3.40 times increased mortality rate (95% CI, 1.5-7.2) than patients infected with a methicillin-susceptible *S. aureus* strain (Engemann, J. J., Carmeli, Y., Cosgrove, S. E., et al. (2003). Adverse Clinical and Economic Outcomes Attributable to Methicillin Resistance among Patients with *Staphylococcus aureus* Surgical Site Infection. *Clinical Infectious Diseases*). Given the health and economic burden attributable, in particular, to SSIs caused by antimicrobial-resistant organisms such as MRSA, there is a critical need for the development of novel treatment options that can address resistant organisms.

SUMMARY OF THE INVENTION

In a first embodiment, the present invention is a device, comprising a base, and a plurality of microneedles attached to the base, wherein the microneedles comprise dehydrated honey having water content of less than 5% by weight.

In a second embodiment, the present invention is a method of fabricating a microneedle device, the device comprising a base, and a plurality of microneedles attached to the base, the method comprising providing a negative mold; applying a liquid comprising a honey and a solvent to the negative mold; exposing the liquid to a negative pressure at a temperature and for a time period sufficient to dehydrate the honey and to thereby form a dehydrated honey, wherein the negative pressure is below atmospheric pressure, and the temperature is below the boiling point of the honey, and further wherein the dehydrated honey has solvent content of less than 5% by weight.

In a third embodiment, the present invention is a system for storing and transporting a microneedle device, comprising at least one device of any one of the aspects of the first embodiment described above and a desiccant.

In a fourth embodiment, the present invention is a method of treating a condition in a subject in need thereof, comprising contacting the subject with a device of any one of the aspects of the first embodiment described above, wherein the condition is an ulcer, a burn wound, an infected wound, a surgical wound, or skin infection.

In a fifth embodiment, the present invention is a method of treating a condition in a subject in need thereof, comprising contacting the subject with a device of any one of the aspects of the first embodiment described above, wherein the condition is a cancer, an inflammatory disease, or an infectious disease.

In a sixth embodiment, the present invention is a method of promoting wound healing in a patient in need thereof, comprising contacting a wound of the subject with a device of any one of the aspects of the first embodiment described above.

BRIEF DESCRIPTION OF THE DRAWINGS

FIG. 4 shows a table containing selected temperature and pressure conditions, which demonstrate the conditions required to achieve the various dehydration states of honey.

FIG. 10 shows a table of the colony counts for each honey preparation in triplicate demonstrating bactericidal properties of Manuka honey at 10% but not at 1%.

FIG. 13 shows plots demonstrating the effect of Manuka honey on wound healing. Analysis of the insert (top) and scratch (bottom) wound-healing assays are shown here. Analysis of the bar graphs of the percent change in wound closure, normalized to time 0 hrs, confirms this significant difference between the cooked honey and the raw and vacuumed honey. In the scratch assay, the vacuumed honey appears to trend towards even faster healing than the control or the other honey preparations.

FIG. 14 shows statistical analysis of wound healing. Paired t-tests for each honey preparation at each time point for both the insert (left) and scratch (right) wound-healing assays were calculated. Values in red have a p-value <0.05 and are considered statistically significant.

FIG. 15 shows an image of an MHM patch. Microneedle dimensions: 300 µm base, 5 µm tip radius, 600 µm height. The MHM was made using a PDMS mold.

DETAILED DESCRIPTION

Figure 1:
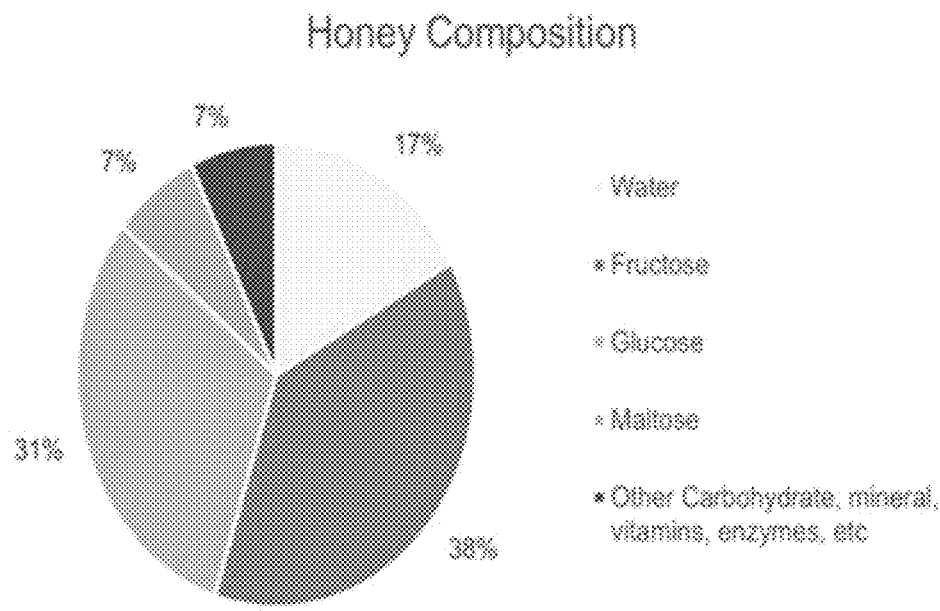
FIG. 1 shows a chart demonstrating the general composition of honey.

Manuka honey is currently FDA-approved and suggested to be effective in MRSA elimination and wound healing. The present disclosure provides devices comprising microneedles, an FDA-approved technique commonly used in dermatological applications to stimulate wound healing and reduce scar formation, to administer Manuka honey for improved healing and MRSA elimination.

Manuka honey comes from New Zealand and Australia. It is harvested by European honeybees (*Apis mellifera*) that have collected pollen primarily from the Manuka tree (*Leptospermum scoparium*). Manuka honey has natural antimicrobial and wound healing properties due to a number of factors, including: high sugar concentration; low pH; anti-myeloperoxidase activity; methylglyoxal (MGO), which has been shown to have non-peroxidase antibacterial activity with effectiveness against some biofilms; Unique Manuka Factor (UMF), a phenolic compound; enzymes, including invertase, amylase, glucose oxidase, and catalase. Additionally, Manuka honey has immunostimulant properties and provides a moist wound healing environment (Rutan, R. (2016). General and Plastic Surgery Panel of the Medical Device Advisory Committee on Classification of Devices; Kwakman P H, to VElde A A, de Boer L, et al. Hoe honey kills bacteria. FASEB, 2010; 24(7):2576-82; Alvarez-Suarez, J., Gasparrini, M., Forbes-Hernandez, T., Mazzoni, L. & Giampieri, F. (2014). The Composition and Biological Activity of Honey: A Focus on Manuka Honey. *Foods*.). Manuka honey has traditionally been used as a holistic treatment for conditions including topical wounds, sore throat, and as an adjunct to cancer treatment (Carter D A, Blair S E, Cokcetin N N, et al. Therapeutic Manuka honey: no longer so alternative. Front Microbiol, 2016, doi.org/10.3389/fmicb.2016.00569; Alvarez-Suarez, J., Gasparrini, M., Forbes-Hernandez, T., Mazzoni, L. & Giampieri, F. (2014). The Composition and Biological Activity of Honey: A Focus on Manuka Honey. *Foods*.). Although once considered "alternative", the many unique medicinal properties of Manuka honey have captured the attention of modern medicine (Carter D A, Blair S E, Cokcetin N N, et al. Therapeutic Manuka honey: no longer so alternative. Front Microbiol, 2016, doi.org/10.3389/fmicb.2016.00569; Minden-Birkenmaier B A, Bowlin G L. Honey-based templates in wound healing and tissue engineering. Bioengineering (Basel), 2018; 5(2):E46). The use of honey in the treatment of infected and non-healing wounds is particularly interesting; especially when honey resistance training studies demonstrate that, at certain concentrations, bacteria do not develop resistance and are incapable of proliferating (Cooper R A, Jenkins L, Henriques A F, et al. Absence of bacterial resistance to medical-grade honey. Eur J Clin Microbiol Infect Dis, 2010; 29(10):1237-41). Manuka honey has been used in medicine for centuries and the first honey-based product for wound dressings was approved by the FDA in 2007 (MEDIHONEY, DermaSciences, Plainsboro, NJ, USA) (Mechcatie, E. (2007). FDA Clears Honey-Based Dressing. *Caring for the Ages*).

Microneedles are a growing tool in the medical community. They are minimally invasive devices that are able to penetrate the skin and assist in drug delivery (Chen M C, Ling M H, Lai K Y, et al. Chitosan microneedle patches for sustained transdermal delivery of macromolecules. Biomacromolecules, 2012; 13(12):4022-31; Gamazo C, Pastor Y, Larraneta E, et al. Understanding the bases of transcutaneous vaccine delivery. Ther Deliv, 2019; 10(1):63-80). In dermatology they have also been shown to promote healing of scar tissue (Biesman B S, Cohen J L, DiBernardo B E, et al. Treatment of atrophic facial acne scars with microneedling followed by polymethylmethacrylate-collagen gel dermal filler. Dermatol Surg, 2019;doi: 10.1097/DSS.0000000000001872; Ibrahim Z A, El-Ashmawy A A, Shora O A. Therapeutic effect of microneedling and autologous platelet-rich plasma in the treatment of atrophic scars: a randomized study. J Cosmet Dermatol, 2017; 16(3)388-399). They are intended to only penetrate about 50-100 µm into the skin, and not stimulate the nerves, enabling application to be painless. While microneedles are commonly made out silicon, metals, ceramics, or silica glass, those made of carbohydrates have several advantages (Park J H, Allen M G, Prausnitz M R. Polymer microneedles for controlled-release drug delivery. Pharm Res, 2006; 23(5): 1008-19). Therapeutically active agents and drugs can be incorporated into the mixture before molding the microneedles, and the microneedles are able to dissolve into the skin after application. While sugars are a common scaffold for microneedle synthesis, honey has not yet been explored as a microneedle building-block or significant component.

Manuka honey is a thixotropic material and has the highest viscosity amongst a range of honeys. The process of dehydrating honey is usually done with high heat, which results in likely damage to the honey's valuable chemicals and enzymes. Dehydration of the honey to a supersaturated sugar solution at hard crack (HC) phase (≤1% moisture content) is essential in the synthesis of microneedle patches, which provides the tensile strength required to penetrate skin (or other tissues), since the HC state's key characteristics are brittleness and rigidity. At this stage the honey's stickiness is at a minimum and it is easier to apply or use as a solid object. The task of dehydrating honey is analogous to candy making.

The present disclosure provides optimized Manuka honey microneedle synthesis, while maintaining the Manuka honey's natural antibacterial and wound-healing properties. In order to reduce the amount of heat required to dehydrate the honey, the present disclosure provides an optimized protocol for moisture content reduction that utilizes low temperature and low pressure (vacuum). Although the vacuum method was successful in bringing the honey to HC, a series of experiments were performed to verify that the most desired properties of the honey were not affected. Through a series of calculations and characterizations, a protocol for the conversion of Manuka honey from a thixotropic liquid to a supersaturated sugar solution with <1% moisture content has been developed, allowing for the molding of the honey into hard microneedles. By using a low pressure and temperature approach, the retained biologic activity of the honey and the detrimental effect of high heat on the honey has been demonstrated. Using this honey-based microneedle synthesis approach, honey can now be used as a primary or adjunct scaffolding component within microneedles, and can potentially be combined with other substances for additive effects. Using this new honey-delivery approach, Manuka honey may now be studied in the context of the treatment of bacterial infections on or below the skin barrier.

MHM patches developed using multiple methods (vacuum treatment, high temperature treatment, also referred to as cooked, and raw) and tested in an in vitro setting are disclosed herein. MHMs were co-incubated with various concentrations of MRSA to evaluate bacterial-killing properties and killing kinetics. The bacterial solutions were then plated and colony formation was evaluated. Fibroblast wound-healing assays were also performed using established human dermal fibroblasts in order to evaluate wound healing properties of various preparations of MHMs.

It was determined that the preparation of the honey has a significant effect on the biologic properties; with high temperatures reducing the antibacterial and wound-healing properties of the honey. By the hard crack (HC) stage, the solution is supersaturated and solidifies at room temperature. During the heating process, a Maillard reaction occurs due to the acidic pH (~4), which results in browning. Heating can also result in the formation of hydroxymethylfurfural (HMF), which has been shown to have potential cytotoxic and mutagenic properties at high concentrations (Janzowski C, Glaab V, Samini E, et al. 5-Hydroxymethylfurfural: assessment of mutagenicity, DNA-damaging potential and reactivity towards cellular glutathione. Food Chem Toxicol, 2000; 38(9):810-9; Severin I, Dumont C, Jondeau-Cabaton A, et al. Genotoxic activities of the food contaminant 5-hydroxymethylfurfural using different in vitro bioassays. Toxicol Lett, 2010; 192(2):189-94; Janini T. Chemistry of honey. The Ohio State University, 2014).

Different concentrations of honey were necessary to achieve the optimal efficacy of wound healing and bacterial killing. The effective concentrations identified in the disclosed experiments are consistent with the previous literature (Ranzato E, Martinotti S, Burlando B. Honey exposure stimulates wound repair of human dermal fibroblasts. Burns Trauma, 2013; 1(1):32-8; Maddocks S E, Lopex M S, Rowlands R S, et al. Manuka honey inhibits the development of *Streptococcus pyogenes* biofilms and causes reduced expression of two fibronectin binding proteins. Microbiology, 2012; 158(Pt 3):781-90; Jenkins R, Burton N, Cooper R. Manuka honey inhibits cell division in methicillin-resistant *Staphylococcus aureus*. J Antimicrob Chemother, 2011; 66(11):2536-42). However, the in vitro concentrations directly translate to the in vivo applications of the MHMs. Several factors should be taken into account, including the rate of honey absorption into the surrounding tissues as well as the interaction with the immune system and local environment. For example, 100% pure Manuka honey applied to various wounds, demonstrates enhanced wound healing and does not show cytotoxicity and progression of the lesion. In the continued development and optimization of MHMs, there may in fact be many formulations that are developed and which are optimal for different use cases, such as a high concentration honey for a contaminated or infected wound versus a low concentration honey for a clean wound (Hixon K R, Bogner S J, Ronning-Arnesen G, et al. Investingating Manuke honey antibacterial properties when incorporated into cryogel, hydrogel, and electrospun tissue engineering scaffolds. Gels, 2019; 5(2):E21; Hilliard G, DeClue C E, Minden-Birkenmaier B A, et al. Preliminary investigation of honey-doped electrospun scaffolds to delay wound closures. J Biomed Mater Res B Biomater, 2019;doi: 10.1002/jbm.b.34351; Negut I, Grumezczscu V, Grumezescu A M. Treatment strategies for infected wounds. Molecules, 2018; 23(9):E2392). Additionally, with the optimization of the MHM manufacturing conditions, such as low pressure and low temperature, other scaffolding materials or additives can be included in the formulation, allowing honey to be a new sugar-base for microneedle synthesis (Neres Santos A M, Duarte Moreira A P, Piler Carvalho C W, et al. Physically cross-linked gels of PVA with natural polymers as matrices for Manuka honey release in wound-care applications. Materials (Basel), 2019; 12(4):E559; Wang M, Hu L, Xu C. Recent advances in the design of polymeric microneedles for transdermal drug delivery and biosensing. Lab on Chip, 2017; 17(8):1373-1387). Future versions of the MHMs can be customized and include other substances or drugs, such as specific antibiotics or aloe vera, for synergistic effects (Liu M Y, Coktein N N, Lu J, et al. Rifampin-manuka honey combinations are superior to other antibiotic-manuka honey combinations in eradicating *Staphylococcus aureus* biofilms. Front Microbiol, 2018; 8:2653; Sing S, Gupta A, Gupta B. Scar free healing mediated by the release of aloe very and Manuka honey from dextran bionanocomposite wound dressings. Int J Biol Macromol, 2018; 120(Pt B):1581-1590).

MHMs disclosed herein demonstrated excellent bactericidal activity against MRSA at concentrations ≥10% of honey, with vacuum-prepared honey appearing to be the most bactericidal, providing killing bacterial concentrations as high as $8\times10^7$ CFU/mL. The wound-healing assay demonstrated that, at concentrations of 0.1%, while the raw and vacuum-prepared honey showed complete wound closure within 24 hours, the cooked honey had incomplete wound closure. The vacuum-treated honey also appeared to have a trend of faster wound closure, as compared to the raw honey.

Production of MHMs.

Manuka Honey Sterile gel (Medihoney, Derma Sciences, Plainsboro, NJ) was used for the synthesis of Manuka honey microneedles (MHMs) disclosed herein. Honey typically has a water concentration of about 17% (FIG. 1) and goes through a number of phase transitions that are described in the making of candy (FIG. 4).

Manuka honey has various active enzymes and chemicals that would be beneficial for the therapeutic applications of the MHMs. Since high heat can have deleterious effects on these compounds, experiments were performed in order to characterize the Manuka honey and determine the pressure that was required to sufficiently dehydrate the honey to form a "hard crack" (HC) stage candy within a microneedle mold. Manuka honey and common table honey were used in these experiments. Dehydration under vacuum was explored in order to avoid the degradation or inactivation of bioactive molecules within the honey that may be heat-sensitive.

Manuka honey is a thixotropic substance, which means that it is a non-Newtonian fluid that has lower viscosity when disturbed, undergoing shearing stresses. Honey is typically transitioned from a liquid form into a solid form through the application of high heat. While there are many ways to transform honey into hard microneedles, two synthesis methods, high temperature treatment ("cooking") and dehydration under reduced pressure ("vacuuming"), have been tested. While evaluating these methods, an assumption was made that the thixotropic properties of the honey are not significant when in low enough quantities and its behavior can still be approximated by Newtonian mechanics.

Figure 2:
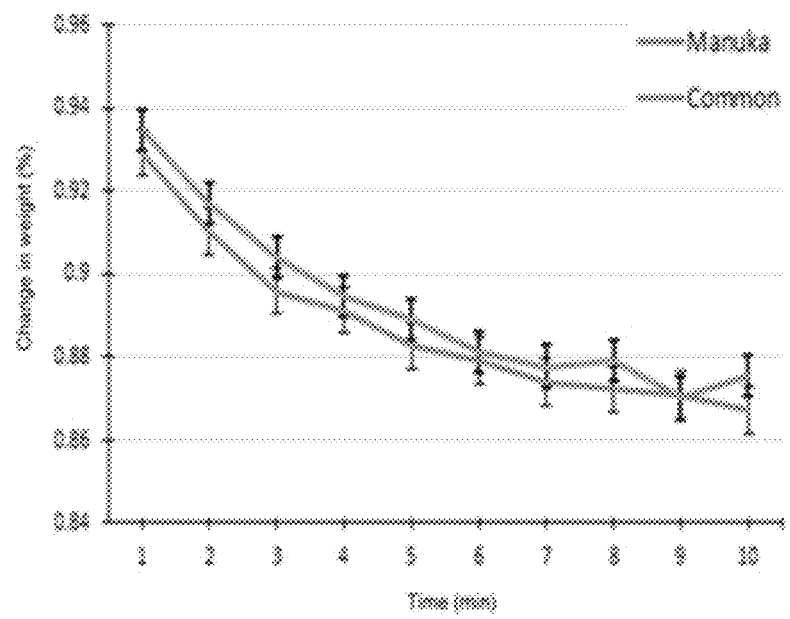
FIG. 2 shows a graph demonstrating the dehydration kinetics of common table honey and Manuka honey over 10 minutes at 80° C.
Figure 3:
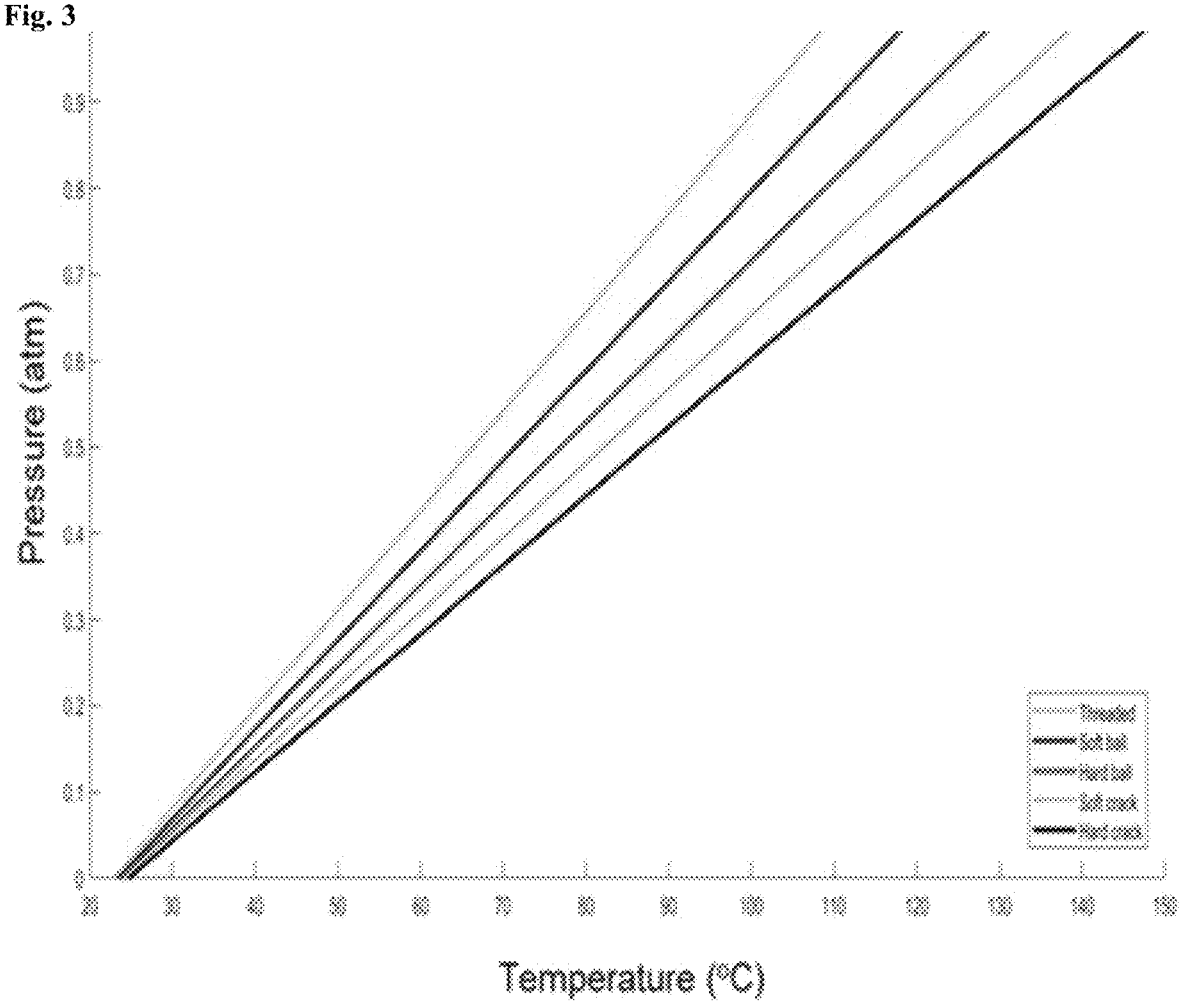
FIG. 3 shows a simulation plot demonstrating the relationship between temperature and pressure to achieve the various stages of honey dehydration.

In order to characterize the percent water composition of the honey, equal volumes of common table honey and Manuka honey were exposed to 80° C. and weighed every minute until they reached the HC phase, i.e., the phase at which most of the moisture content is assumed to be gone (FIG. 2). Achievement of the HC phase was determined by placing the honey in cool water and then applying pressure to the honey, demonstrating hardness, lack of deformability, and a "crack" when enough pressure was applied. This information was then used to calculate the pressure that the honey would need to be exposed to at various temperatures in order to achieve HC (FIG. 3).

Through the use of the Clausius-Clapeyron equation, it was estimated that the approximate pressure that would be necessary to boil water at 40° C. would be around 10% of what is necessary for water to boil at the room temperature.

Clausius-Clapeyron Eqn:

$$\ln\left(\frac{P_2}{P_1}\right) = \frac{-\Delta H_{vapor}}{R}\left(\frac{1}{T_2} - \frac{1}{T_1}\right) \quad (1)$$

Solving for $P_2$ which represents the final pressure.

$$P_2 = P_1 e^{\frac{-\Delta H_{vapor}}{R}\left(\frac{1}{T_2}-\frac{1}{T_1}\right)} \quad (2)$$

The moles of water and sugar are then used to calculate the molar fraction of water in the honey.

$$X_{H_2O} = \frac{\text{moles H}_2\text{O}}{\text{moles sugar} + \text{moles H}_2\text{O}} \quad (3)$$

This molar fraction of water is then applied to Raoult's law in order to calculate the pressure required to reach the boiling point of the honey.

$$P_{Honey,Boiling} = X_{H_2O} \times P_{H_2O,Boiling}^O \quad (4)$$

From this equation it was deduced that, as the concentration of water in honey decreases through boiling, the pressure that the honey is under also has to decrease to be low enough for the honey to continue boiling. This estimation provided the starting dehydration pressure and was used to estimate the temperature and pressure combinations that would be required to produce HC MHMs. For the initial pressure and temperature variation experiments, a TECA® hotplate and a desiccator with a RS1.5 4CFM vacuum pump (Emerald Gold®) were used. Once the protocol was optimized, a NAPCO® Vacuum oven (Model 5831) with manually-set temperature and pressure settings was used.

Figure 5:
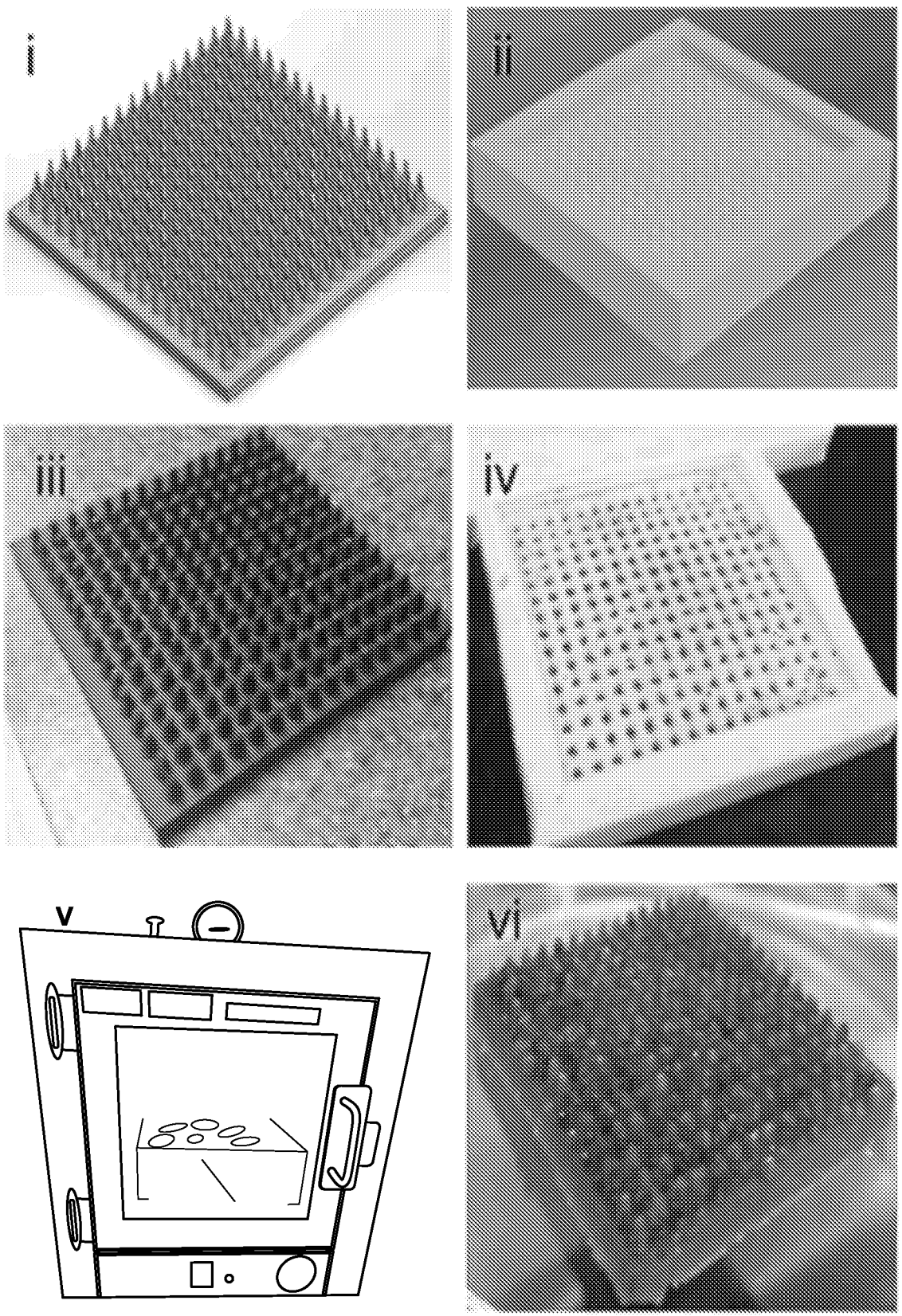
FIG. 5 shows Autocad® rendering of the microneedle molds (i-ii) with their respective 3D-printed (iii) and elastomer negative mold (iv). The vacuum oven (v) used to make the honey microneedles (vi) is also shown. These molds, although functional, resulted in uneven dehydration rates and asymmetrical microneedles.
Figure 6:
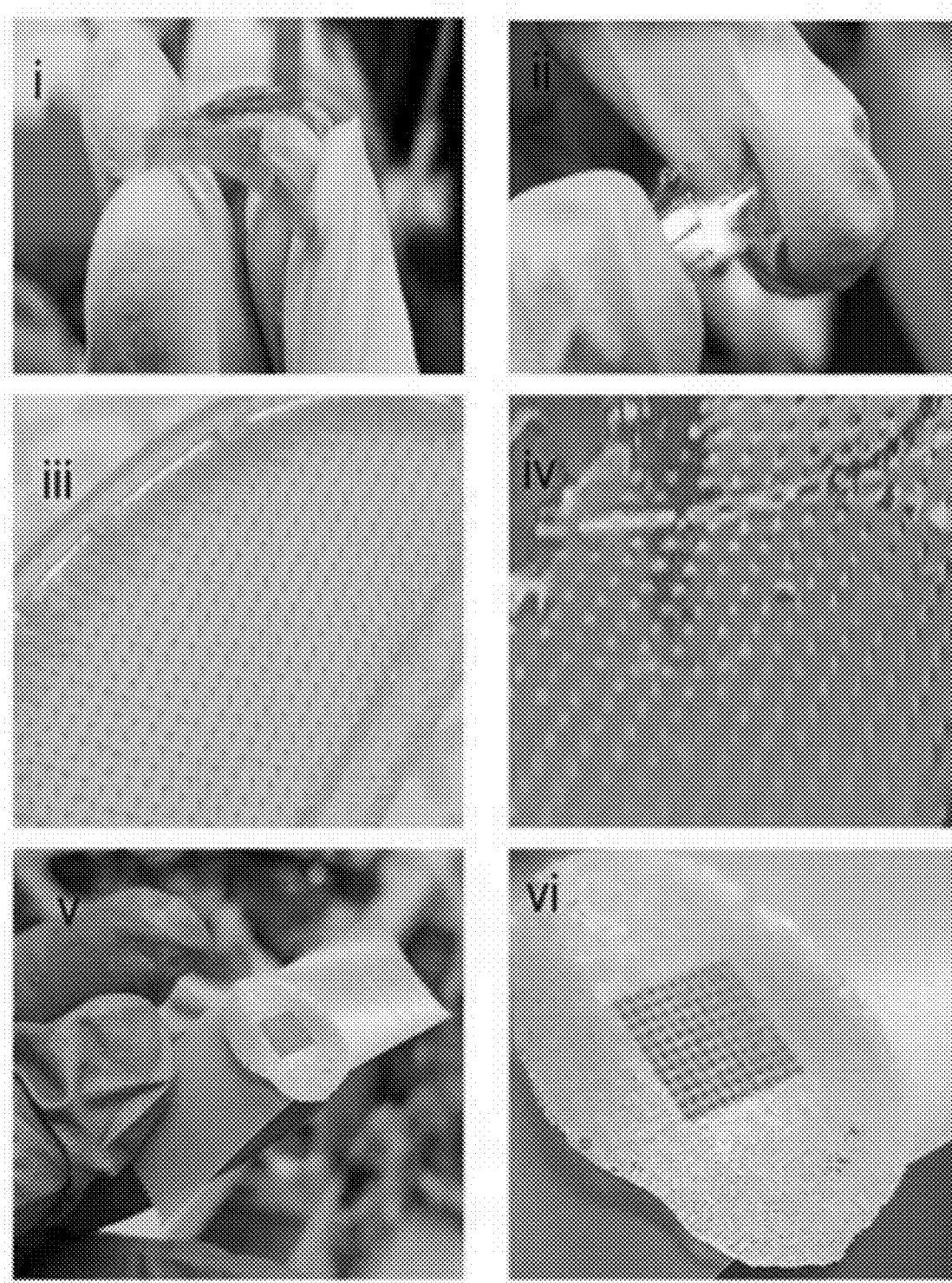
FIG. 6 shows PDMS used as a mold for Manuka Honey Microneedles (MHM) production, which allowed for fine feature formation and ease of honey removal (i-ii). Microneedle molds were made from two commercially-available microneedle patches using PDMS, and both resulted in fine and even microneedles (iii-vi).

The obtained information was used to create MHMs using both custom and commercially-available microneedle molds. In order to make the in-house microneedle molds, AutoCad® (Autodesk, San Rafael, CA) was used to create a microneedle match 3D, and the negative mold was derived from the positive mold (FIG. 5). The positive mold was printed in acrylonitrile butadiene styrene (ABS), using Stratasys uPrint® 3D printer (Prairie, MN). The positive mold was then used to make a negative mold out of silicon. This negative mold was used in experiments for the testing and optimization of the temperature and pressure combinations for transforming the honey into the HC phase within a mold. Once the mold formation was optimized, the MHM formation protocol was tested using smaller molds made of polydimethylsiloxane-diacrylamide (PDMS, Sylgard™ Silicone Elastomer Kit, DOW Corning, Midland, MI) (FIG. 6). The PDMS mold allowed for the creation of smaller features and easy removal of the MHMs from the negative mold. For the PDMS molds, one in-house negative mold was created using a commercially-available microneedle patch as the positive mold (Hyaluronic Acid Micro Needle Patch, WELLAGE), and a microneedle negative PDMS mold was purchased from Blueacre Technology (Co Louth, Ireland). The commercial PDMS mold had the following parameters: 11×11 array with 600 μm height, 300 μm base diameter, and 5 μm tip radius. The final conditions for the cooked- and vacuum-prepared preparations were 165° C. at 1 atm, and 40° C. at 0.16 atm for 20 hours, respectively. The honey was placed onto the negative mold and then placed in the temperature-controlled vacuum oven or on a hot plate and then immediately into a vacuum chamber in order to draw the honey into the negative needle mold.

Bacterial Killing Assay

Figure 7:
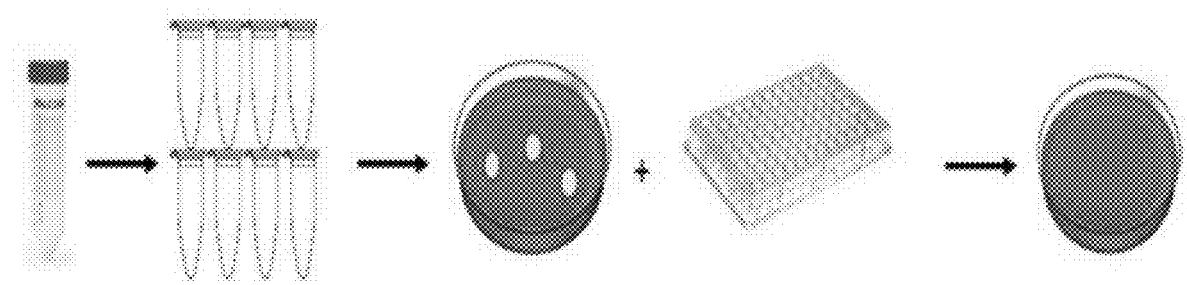
FIG. 7 shows a flow diagram of the experimental set-up for the co-culture of MRSA bacteria and Manuka honey preparations. First the bacteria and honey preparations are mixed and serial dilutions are made. One aliquot of the resulting solutions plated to verify growth and purity of the bacterial culture and the other aliquot is seeded in a 96-well plate for overnight culture. The following day, these are plated and cultured overnight.
Figure 8:
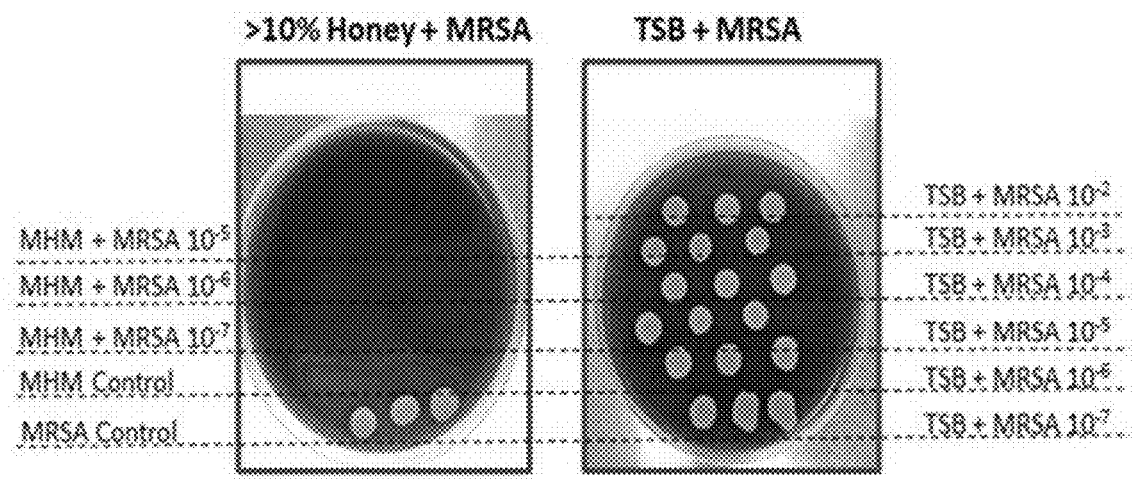
FIG. 8 shows representative photographs of a >10% Manuka honey positive control on the left and a negative control, TSB only, on the right. As expected, there is no growth in the honey preparation but there is copious growth in the negative control.
Figure 9:
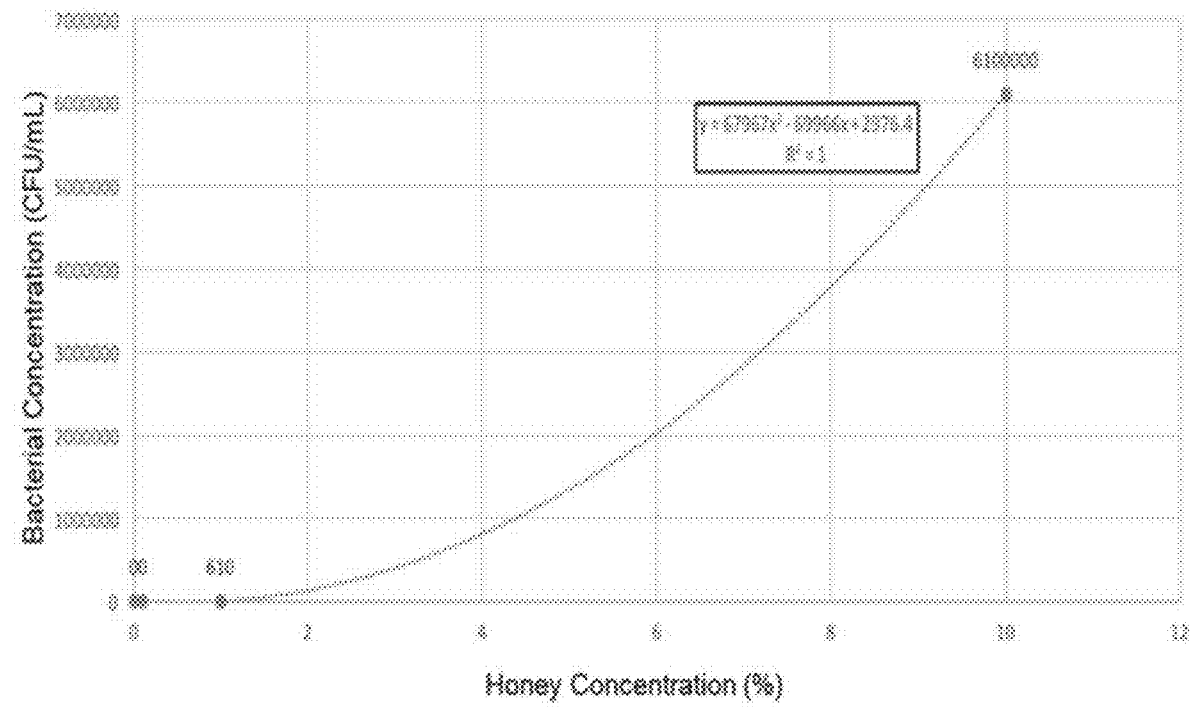
FIG. 9 shows a bacterial killing curve based on the 24-hour colony counts of various concentrations of Manuka honey and MRSA.

Honey solutions prepared in different ways were assessed in a bacterial killing assay (FIG. 7). After 24 hours of MRSA and honey co-incubation, it was determined that the honey preparation method had an effect on the bacterial-killing capabilities of the honey (FIG. 8). A raw honey bacterial killing curve was first evaluated (FIG. 9), where multiple concentrations of raw Manuka honey were co-incubated with MRSA bacteria, and then colonies were counted after a second 24-hour incubation. Based on best-fit line equation, 10% and 1% raw Manuka honey were expected to start having bacterial-killing properties at about 6×10$^6$ CFU/mL and 6.1×10$^2$ CFU/mL, respectively. The positive control for the experiments was 50% raw Manuka honey, which killed all bacteria after a 24-hour incubation period. The experimental results of MRSA assay show that all 10% honey preparations start killing bacteria at about 8×10$^4$ CFU/mL, with the vacuumed honey having variable killing results up to 8×10$^7$ CFU/mL (FIG. 10). These results suggest that: at least a 10% honey concentration is needed for bactericidal effects on MRSA; there is an initial bacterial-concentration-relationship; and the vacuumed honey preparation may have more potent bactericidal effects than the raw and cooked honey preparations.

Wound Healing Assay

Figure 12:
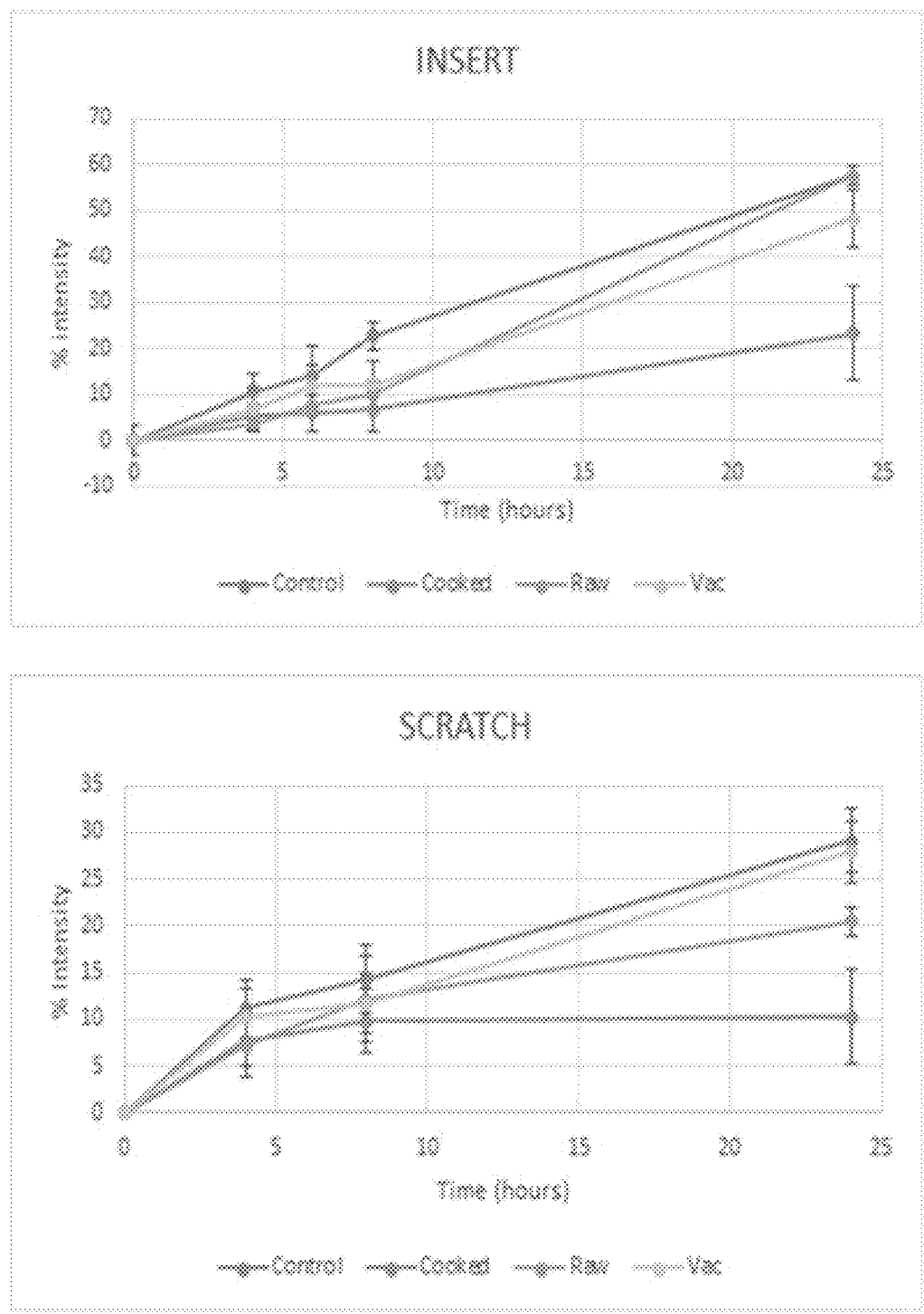
FIG. 12 shows plots demonstrating the effect of Manuka honey on wound healing. Analysis of the insert (top) and scratch (bottom) wound-healing assays are shown. A line graph showing the mean with the standard deviation for each condition demonstrates that the cooked honey preparation provided significantly less closure than the raw and vacuumed preparations. In the scratch assay, the vacuumed honey appears to trend towards even faster healing than the control or the other honey preparations.

The effects of various preparations of honey on two wound healing assays, scratch and insert assays, were assessed. Earlier experiments confirmed that high concentrations of honey (>1%) appear to be cytotoxic, while concentrations ≤0.1% appear to be safe. This observation is consistent with previous literature; therefore, 0.1% honey concentration was used for this set of experiments. Two assays were performed in order to assess the differences, if any, in the effects of the honey on an assay that contains cell-injury markers. In the scratch assay, cell-injury markers were released as a results of the physical scraping and cell damage of the pipette tip; while in the insert assay, simple cell migration model without the cell injury markers is evaluated. Both the insert and scratch assay models demonstrated significantly reduced wound-gap closure when cooked honey were used (FIGS. 12-14). In the scratch assay, the vacuum-prepared honey appears to show a trend towards faster wound gap closure compared to both cooked and raw honey. These results demonstrate that the preparation of honey has an effect on the wound-healing properties of the honey and that high temperature treatment can degrade the beneficial proteins and other compounds in the honey and be detrimental to wound healing.

Immuno-Stimulatory Properties of MHMs

Figure 16:
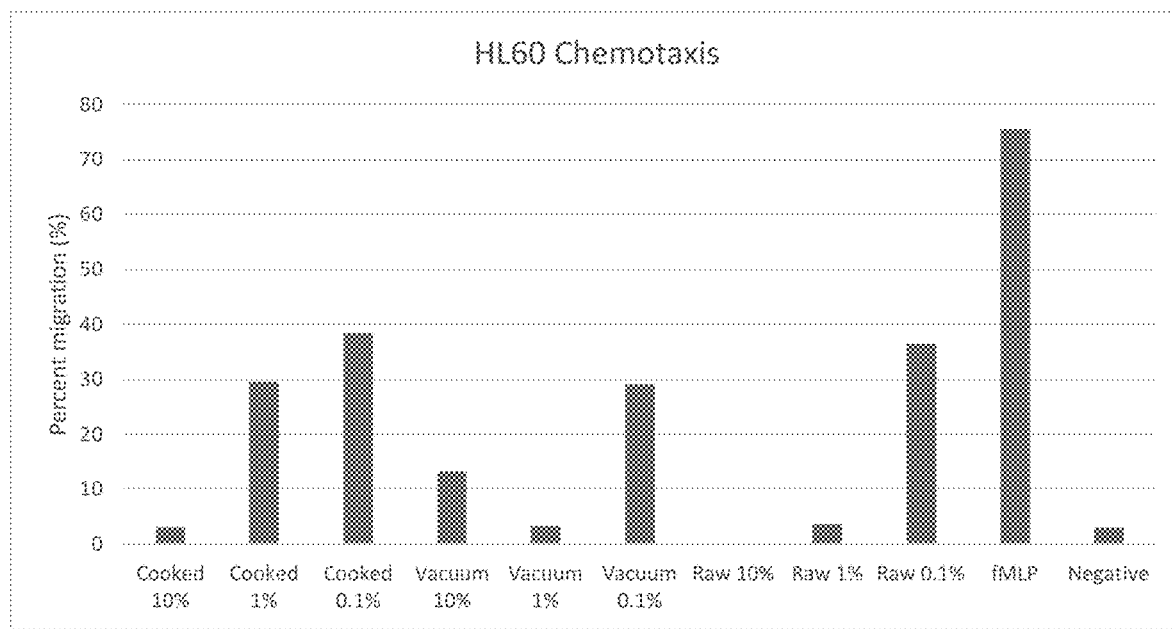
FIG. 16 shows a bar graph demonstrating induction of chemotaxis in HL60 cells differentiated into neutrophils in the presence of 0.1%, 1%, and 10% honey solutions generated from different honey preparations.

Various honey preparations were prepared in disc shape in either vacuum or cooked conditions and then these discs were dissolved into solutions. 10%, 1%, and 0.1% honey solutions were co-incubated with HL60 cells differentiated into neutrophils with DMSO. Transwell plates with 3 μm pores were equilibrated with the honey solution, negative control (media only) or positive control (100 nM N-Formyl-Met-Leu-Phe (fMLP)). HL60 cells were seeded onto the transwell membrane, incubated for 4 hours and then cells that had migrated to the bottom of the transwell were counted with a hemacytometer. The results of the experiments are shown in FIG. 16.

The obtained data show the following:
each of the examined honey preparations containing 10% of honey showed no increase in chemotaxis and may have shown some cytotoxicity;
each of the examined honey preparations containing 1% of honey provided increase or no change in chemotaxis; and
each of the examined honey preparations containing 0.1% honey gave the most consistent increase in chemotaxis.

These results are consistent with the findings of the effects of the MHM preparations on fibroblast migration and also demonstrate that MHMs may have immunomodulatory effects, with potential leukocyte recruitment at low concentrations.

The demonstrated immuno-stimulatory properties of MHMs will allow the use of MHMs to turn immunologically "cold" tumors into "hot" ones. Immunologically cold tumors are cancers that for various reasons contain few infiltrating T cells and are not recognized and do not provoke a strong response by the immune system, making them difficult to treat with current immunotherapies. Cancers that are classically immunologically cold include glioblastomas as well as ovarian, prostate, pancreatic, and most breast cancers. In contrast, immunologically hot tumors contain high levels of infiltrating T cells and more antigens, making them more recognizable by the immune system and more likely to trigger a strong immune response. Due to the immuno-stimulatory properties of the MHMs, application of MHMs to cold tumors will activate T cell infiltration of the tumors, turning them hot.

MHM Preparations Containing Phages.

MHM patched can be formulated to contain additional active pharmaceutical ingredients. For example, phages can be added to the honey in order to obtain the beneficial impacts of phage—honey combinations against bacterial cells. The synergistic effect of the phage honey combination has been previously demonstrated and is attributed to the antiviral effect of honey which limits the emergence of phage resistant phenotypes.

Before the discovery of modern antibiotics, bacteriophages (phages) and bee hive products such as honey were extensively used for their antimicrobial properties. Phages are harmless to mammalian cells and are specific for a target bacterium, therefore do not affect the commensal microflora. In contrast with antibiotics, phages have the ability to self-replicate as long as the host is present, which implies that a single dose is sufficient.

Reports assessing the effectiveness of phages and antibiotics on wounds show that postoperative wound infections in cancer patients and also postsurgical wounds had a higher healing success with phage. Another attractive characteristic is that phages can destroy, to varying extent, mono and mixed biofilm populations. Studies have shown that application of combined phage-honey formulations to biofilms resulted in higher efficacies than application of phages alone, possibly due to honey's capacity to damage the bacterial cell membrane and also to its ability to penetrate the biofilm matrix, promoting and enhancing the subsequent phage infection.

MHMs containing phages can be particularly advantageous for treatment of infections such as tuberculosis, where the microneedles can be used to penetrate through the skin granuloma and inject the phage/honey therapy.

MHM Preparations Containing Stabilized Proteins.

Honey has been shown to stabilize proteins, such as bovine serum albumin (BSA). Protein-stabilizing properties of honey make MHMs an especially attractive vehicle for delivery of protein-containing active pharmaceutical ingredients (APIs), since MHMs disclosed herein can be manufactured without application of high heat, thus avoiding damage to the protein cargo.

In a first embodiment, the present invention is a device, comprising a base, and a plurality of microneedles attached to the base, wherein the microneedles comprise dehydrated honey having water content of less than 5% by weight.

Honey is a sweet, viscous substance produced by bees and some related insects. Honey is produced from the sugary secretions of plants (floral nectar) by regurgitation, enzymatic activity, and water evaporation, and is stored in wax structures called a honeycomb. The most commonly commercially available varieties of honey are produced by honey bees (the genus Apis). Any honey can be used in the practice of the inventions defined herein.

In a first aspect of the first embodiment, the base of the devices also comprises dehydrated honey having water content of less than 5% by weight. For example, the dehydrated honey can have water content of not greater than 4.5%, not greater than 4%, not greater than 3.5%, not greater than 3%, not greater than 2.5%, not greater than 2%, not greater than 1.5%, not greater than 1%, or not greater than 0.5%.

In a second aspect of the first embodiment, the microneedles further include a water-soluble polymer material, wherein the polymer material is mixed with the dehydrated honey. Examples of suitable polymer materials include poly(vinyl alcohol) (PVA), poly(vinylpyrrolidone) (PVP), dextran, carboxymethyl cellulose (CMC), chondroitin sulfate, and sugars. Other examples include: Sodium hyaluronate, Gantrez® AN-139, Gantrez® AN-139 and polysorbate 80, Sucrose and threonine, Maltodextrin, Sucrose, threonine and CMC, Na-CMC and trehalose, Na-CMC, sucrose and lactose, poly(acrylic acid) (PAA), Sodium chondroitin sulfate, Chitosan, Trehalose and PVA, Dextran 70 and sorbitol, Fish gelatin and sucrose, and PVA and sucrose.

In a third aspect of the first embodiment, the microneedles include a scaffold material, wherein the scaffold material is coated with the dehydrated honey. In various aspects, for non-dissolving microneedles materials, the honey can be either coated on top, or the needle may have a hollow area connecting to the tip, with the dehydrated honey occupying the hollow area.

In various aspects, the scaffold material can be a plastic or a metal. For example, the scaffold material can be a sugar. Scaffold material can be of a dissolving material (example: sugar-based or other biodegradable material), or non-dissolving (example: polymer, silicon, metal, glass, carbon, silk or other).

In a fourth aspect of the first embodiment, the microneedles are composed of (for example, made out of) the dehydrated honey.

In a fifth aspect of the first embodiment, the base is composed of the dehydrated honey.

In a sixth aspect of the first embodiment, the dehydrated honey has water content of not greater than 1% by weight.

In a seventh aspect of the first embodiment, the device includes at least one additional active pharmaceutical ingredient (API).

In an eighth aspect of the first embodiment, the additional API is selected from a phage, an antiviral agent, an antifungal agent, an anti-parasitic agent, an antibacterial agent, a chemotherapeutic agent, an antibody, a cytokine, a growth factor, hormone, a vaccine, a nucleic acid, a nucleic acid modifying agent, a nutraceutical agent, an anesthetic, a sedative, or a narcotic-blocking or narcotic-reversing agent. For example, the additional API can be selected from an antiviral agent, an antifungal agent, an anti-parasitic agent, an antibacterial agent, a cytokine, a growth factor, a hormone, a vaccine, a nucleic acid modifying agent, an anesthetic, a sedative, or an opioid-blocking agent.

Examples of vaccine APIs include, but are not limited to live virus vaccines (such as MMR vaccine and the varicella vaccine), killed (inactivated) vaccines (such as pertussis vaccine), toxoid vaccines (such as diphtheria and tetanus vaccines), and biosynthetic vaccines (such as Hepatitis B vaccine). For example, a vaccine can be selected from a varicella vaccine, a DTaP vaccine, a Hepatitis A vaccine, a Hepatitis B vaccine, a Hib vaccine, an HPV vaccine, an Influenza vaccine, a Meningococcal vaccine, an MMR vaccine, a Pneumococcal conjugate vaccine, a Pneumococcal polysaccharide vaccine, a Rotavirus vaccine, a Tdap vaccine, a rabies vaccine, a Zika virus vaccine, and a Tetanus vaccine. Alternatively, a vaccine can include microRNA.

Examples of chemotherapeutic agents that are used in the treatment of neoplastic disorders include, but are not limited to, doxorubicin, carboplatin, cyclophosphamide, daunorubicin, epirubicin, 5-fluorouracil, gemcitabine, eribulin, ixabepilone, methotrexate, mutamycin, mitoxantrone, vinorelbine, paclitaxel, docetaxel, thiotepa, vincristine, and capecitabine.

Examples of antibodies include, but are not limited to, abciximab, adalimumab, alefacept, alemtuzumab, basiliximab, belimumab, bezlotoxumab, canakinumab, certolizumab pegol, cetuximab, daclizumab, denosumab, efalizumab, golimumab, inflectra, ipilimumab, ixekizumab, natalizumab, nivolumab, olaratumab, omalizumab, palivizumab, panitumumab, pembrolizumab, rituximab, tocilizumab, trastuzumab, secukinumab, and ustekinumab.

As used herein, "nutraceutical agent" refers to a product isolated or purified from foods that is generally sold in medicinal forms not usually associated with food is demonstrated to have a physiological benefit or provide protection against chronic disease. Examples of nutraceutical agents include, but are not limited minerals, vitamins, herbal products (such as garlic, ginger, echinacea, ginseng, liquorice, onion, and senna, turmeric), dietary enzymes (such as bromelain and papain), hydrolyzed proteins, phytonutrients (such as resveratrol), and carotenoids (such as lycopene).

In various aspects, the additional API could be a supplement such as aloe vera, chondroitin sulfate, or a green tea extract. An anesthetic can be lidocaine or bupivacaine. A narcotic-blocking or narcotic-reversing agent can be an opioid-blocking agent, such as naloxone.

Examples of the additional APIs include clotrimazole, econazole, miconazole, terbinafine, fluconazole, ketoconazole, amphotericin, acyclovir, cefazolin, a penicillin, a tetracyclines, a cephalosporins, a quinolone, a lincomycin, a macrolide, a sulfonamide, a glycopeptide, an aminoglycoside, a carbapenem; an interleukin, such as IL-10, an Interferon, such as IFN-alpha, a TNF, such as TNF-alpha, a TGF-β, such as TGF-β1, a hematopoietin, such as EPO (further examples of which are provided in https://www.ncbi.nlm.nih.gov/books/NBK6294/table/A13506/?report=objectonly), incorporated herein by reference. Examples of the additional APIs further include Adrenomedullin (AM), Angiopoietin (Ang), Autocrine motility factor, Bone morphogenetic proteins (BMPs), Ciliary neurotrophic factor family, Ciliary neurotrophic factor (CNTF), Leukemia inhibitory factor (LIF), Colony-stimulating factors, Macrophage colony-stimulating factor (M-CSF), Granulocyte, colony-stimulating factor (G-CSF), Granulocyte macrophage colony-stimulating factor (GM-CSF), Epidermal growth factor (EGF), Ephrins, Fibroblast growth factor (FGF), Fetal Bovine Somatotrophin (FBS), GDNF family of ligands, Glial cell line-derived neurotrophic factor (GDNF), Neurturin, Persephin, Artemin, Growth differentiation factor-9 (GDF9), Hepatocyte growth factor (HGF), Hepatoma-derived growth factor (HDGF), Insulin, Insulin-like growth factors, Insulin-like growth factor-1 (IGF-1), Insulin-like growth factor-2 (IGF-2), Macrophage-stimulating protein (MSP), also known as hepatocyte growth factor-like protein (HGFLP), Myostatin (GDF-8), Neuregulins, Neurotrophins, Brain-derived neurotrophic factor (BDNF), Nerve growth factor (NGF), Neurotrophin-3 (NT-3), Neurotrophin-4 (NT-4), Placental growth factor (PGF), Platelet-derived growth factor (PDGF), Renalase (RNLS), T-cell growth factor (TCGF), Thrombopoietin (TPO), Transforming growth factors, Vascular endothelial growth factor (VEGF).

In various aspects, DNA or RNA modifying agents include mRNA, siRNA, double-stranded RNA, CRISPR-employing nucleic acid modified agents, etc.

In various aspects, a sedative includes a Barbiturate, a Benzodiazepine, a Nonbenzodiazepine hypnotic, an Orexin antagonist, an Antihistamine, a General Anesthetic, an Herbal sedative, a Methaqualone and analogues, a Skeletal Muscle Relaxant, an Opioid, an Antidepressant, or an Antipsychotic.

In a ninth aspect of the first embodiment, the additional API is a peptide or a protein.

In a tenth aspect of the first embodiment, the device can further include a substrate layer disposed on the base.

In an eleventh aspect of the first embodiment, the dehydrated honey is a dehydrated Manuka honey.

Manuka honey is a monofloral honey produced from the nectar of the manuka tree, *Leptospermum scoparium*. It is typically produced by European honey bees (*Apis mellifera*) foraging on the manuka or tea tree (*Leptospermum scoparium*) which grows uncultivated throughout New Zealand and southeastern Australia. An example of Manuka honey suitable for practicing the present invention is a product branded Medohoney® available from Dermasciences, http://www.dermasciences.com/medihoney.

In a second embodiment, the present invention is a method of fabricating a microneedle device, the device comprising a base, and a plurality of microneedles attached to the base, the method comprising providing a negative mold; applying a liquid comprising a honey and a solvent to the negative mold; exposing the liquid to a negative pressure at a temperature and for a time period sufficient to dehydrate the honey and to thereby form a dehydrated honey, wherein the negative pressure is below atmospheric pressure, and the temperature is below the boiling point of the honey, and further wherein the dehydrated honey has solvent content of less than 5% by weight. In certain embodiments, the liquid comprising honey is a liquid consisting essentially of honey; in other aspects, it is an aqueous solution of honey; in yet other aspects the liquid is a solvent resuspension of dehydrated honey, where the solvent can be water.

"Solvent," as used herein, refers to a single solvent or a mixture of two or more (typically, two) different solvents. Exemplary solvents include water and organic solvents such as, but not limited to, methanol, ethanol, diisopropyl ether, isopropanol, ethyl acetate, and isopropyl acetate. In certain embodiments, solvents of the present invention are solvents that dissolve honey.

"Alcohol," as used herein, refers to an organic compound in which the hydroxyl functional group is bound to a carbon. Exemplary alcohols include, but are not limited to methanol, ethanol, 1-propanol, isopropanol, 1-butanol, 2-butanol, neopentyl alcohol, isooctanol, isoamyl alcohol, cyclohexanol, methyl cyclohexanol, ethylene glycol, and diethylene glycol.

In second aspect of the second embodiment, the liquid is an aqueous solution; the solvent is water; and drying the honey is dehydrating the honey, thereby forming dehydrated honey. In certain aspects, the present invention is a method of fabricating a microneedle device, the device comprising a base, and a plurality of microneedles attached to the base, the method comprising providing a negative mold; applying an aqueous solution comprising a honey to the negative mold; exposing the liquid to a negative pressure at a temperature and for a time period sufficient to dehydrate the honey and to thereby form a dehydrated honey, wherein the negative pressure is below atmospheric pressure, and the temperature is below the boiling point of the honey, and further wherein the dehydrated honey has water content of less than 5% by weight.

In a third aspect of the second embodiment, the negative pressure is less than 1 atm, the temperature is not greater than 80° C., and the time is not greater than 48 hours.

In a fourth aspect of the second embodiment, the negative pressure is less than 1 atm, not greater than 0.9 atm, not greater than 0.8 atm, not greater than 0.7 atm, not greater than 0.6 atm, not greater than 0.5 atm, not greater than 0.4 atm, not greater than 0.3 atm, not greater than 0.2 atm, or not greater than 0.1 atm; the temperature is not greater than 80° C., not greater than 70° C., not greater than 60° C., not greater than 50° C., not greater than 40° C., not greater than 30° C., or not greater than 20° C.; and the time is not greater than 48 hours, not greater than 42 hours, not greater than 36 hours, not greater than 30 hours, not greater than 24 hours, not greater than 20 hours, not greater than 14 hours, or not greater than 8 hours.

In a fifth aspect of the second embodiment, the negative pressure is from 0.001 atm to 0.5 atm, the temperature is from 20° C. to 60° C., and the time is from 6 hours to 36 hours.

In a sixth aspect of the second embodiment, the negative pressure is from 0.1 atm to 0.2 atm, the temperature is from 35° C. to 45° C., and the time is from 18 hours to 24 hours.

In a seventh aspect of the second embodiment, the dehydrated honey has water content of less than 5% by weight, not greater than 4.5%, not greater than 4%, not greater than 3.5%, not greater than 3%, not greater than 2.5%, not greater than 2%, not greater than 1.5%, not greater than 1%, or not greater than 0.5%.

In an eighth aspect of the second embodiment, the liquid includes a polymer material, wherein the polymer material is dissolved in the liquid.

In a ninth aspect of the second embodiment, the polymer material is water soluble.

In a tenth aspect of the second embodiment, the method further includes the step of dipping a scaffold material in the aqueous solution, thereby producing the microneedle device comprising the scaffold material coated with the dehydrated honey.

In an eleventh aspect of the second embodiment, the aqueous solution is the honey.

In a twelfth aspect of the second embodiment, the dehydrated honey has water content of not greater than 1% by weight.

In a thirteenth aspect of the second embodiment, the aqueous solution includes at least one additional active pharmaceutical ingredient (API)

In a fourteenth aspect of the second embodiment, the additional API is selected from a phage, an antiviral agent, an antifungal agent, an anti-parasitic agent, an antibacterial agent, a chemotherapeutic agent, an antibody, a cytokine, a growth factor, a hormone, a vaccine, a nucleic acid, a nucleic acid modifying agent, a nutraceutical agent, an anesthetic, a sedative, a narcotic-blocking, and narcotic-reversing agent. For example, the API can be selected from an antiviral agent, an antifungal agent, an anti-parasitic agent, an antibacterial agent, a cytokine, a growth factor, hormone, a vaccine, a nucleic acid modifying agent, an anesthetic, a sedative, and an opioid-blocking agent.

In a fifteenth aspect of the second embodiment, the API is a peptide or a protein.

In a sixteenth aspect of the second embodiment, the method further includes the step of including attaching a substrate layer to the base.

In a seventeenth aspect of the second embodiment, the honey is a Manuka honey.

In a third embodiment, the present invention is a system for storing and transporting a microneedle device, comprising at least one device of any one of the aspects of the first embodiment described above and a desiccant. In various aspects, the system for storing and transporting a microneedle device can further comprise an inert gas, such as nitrogen or argon.

A desiccant is a hygroscopic substance used as a drying agent. Any commonly suitable desiccants can be used, for example, chemically inert and non-toxic substances such as silica, activated charcoal, calcium sulfate, calcium chloride, and zeolites.

As used herein, "subject" and "patient" may be used interchangeably, and they mean to treat a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

As used herein, "treating" or "treatment" means obtaining a desired pharmacological and/or physiological effect. The effect can be prophylactic or therapeutic, which includes achieving, partially or substantially, one or more of the following results: partially or totally reducing the extent of the disease, disorder or syndrome; ameliorating or improving a clinical symptom or indicator associated with the disorder; delaying, inhibiting or decreasing the likelihood of the progression of the disease, disorder or syndrome; or partially or totally delaying, inhibiting or reducing the likelihood of the onset or development of disease, disorder or syndrome.

The term "treat" means decrease, suppress, attenuate, diminish, arrest, or stabilize the development or progression of a disease (e.g., a disease or disorder delineated herein), lessen the severity of the disease or improve the symptoms associated with the disease.

In a fourth embodiment, the present invention is a method of treating a condition in a subject in need thereof, comprising contacting the subject with a device of any one of the aspects of the first embodiment described above, wherein the condition is an ulcer, a burn wound, an infected wound, a surgical wound, or skin infection.

In a fifth embodiment, the present invention is a method of treating a condition in a subject in need thereof, comprising contacting the subject with a device of any one of the aspects of the first embodiment described above, wherein the condition is a cancer, an inflammatory disease, or an infectious disease. In various aspects, the infectious disease can be a local infectious disease or a systemic infectious disease.

In the first aspect of the fifth embodiment, the cancer is selected from breast cancer, lung cancer, skin cancer, hemangiosarcoma, splenic cancer, stomach cancer, liver cancer, colorectal cancer, gallbladder cancer, pancreatic cancer, prostate cancer, ovarian cancer, kidney cancer, osteosarcoma, stromal tumor, and bladder cancer. For example, breast cancer can be selected from invasive or non-invasive ductal or lobular carcinoma, tubular, medullary, mucinous, papillary, cribriform carcinoma of the breast, male breast cancer, recurrent or metastatic breast cancer, phyllodes tumor of the breast, and Paget's disease of the nipple; lung cancer can be selected from small cell lung cancer, bronchial carcinoids, and non-small cell lung cancer, such as adenocarcinoma, squamous cell carcinoma, and large cell carcinoma; liver cancer can be selected from hepatocellular carcinoma, colangiocarcinoma, and angiosarcoma; and skin cancer can be selected from melanoma, basal cell carcinoma, and squamous cell carcinoma.

In the second aspect of the fifth embodiment, the inflammatory disease is selected from multiple sclerosis, rheumatoid arthritis, degenerative joint disease, systemic lupus, systemic sclerosis, small vessel vasculitis syndrome, medium small vessel vasculitis syndrome, large small vessel vasculitis syndrome, atherosclerosis, inflammatory bowel disease, irritable bowel syndrome, Crohn's disease, mucous colitis, ulcerative colitis, gastritis, sepsis, dermatological inflammatory disorder, and urticarial syndromes. For example, a dermatological inflammatory disorders can be selected from psoriasis, eczema, atopic dermatitis, contact dermatitis, urticaria, scleroderma, dermatosis with acute inflammatory components, pemphigus, pemphigoid, and allergic dermatitis.

In the third aspect of the fifth embodiment, the infectious disease is selected from a bacterial infectious disease, a fungal infectious disease, and a viral infectious disease.

In certain aspects, a viral infectious disease includes, but is not limited to, a disease selected from acute febrile pharyngitis, pharyngoconjunctival fever, epidemic keratoconjunctivitis, infantile gastroenteritis, Coxsackie infections, infectious mononucleosis, Burkitt lymphoma, acute hepatitis, chronic hepatitis, hepatic cirrhosis, hepatocellular carcinoma, primary HSV-1 infection (e.g., gingivostomatitis in children, tonsillitis and pharyngitis in adults, keratoconjunctivitis), latent HSV-1 infection (e.g., herpes labialis and cold sores), primary HSV-2 infection, latent HSV-2 infection, aseptic meningitis, infectious mononucleosis, Cytomegalic inclusion disease, Kaposi's sarcoma, multicentric Castleman disease, primary effusion lymphoma, AIDS, influenza, Reye syndrome, measles, postinfectious encephalomyelitis, Mumps, hyperplastic epithelial lesions (e.g., common, flat, plantar and anogenital warts, laryngeal papillomas, epidermodysplasia verruciformis), cervical carcinoma, squamous cell carcinomas, croup, pneumonia, bronchiolitis, common cold, Poliomyelitis, Rabies, influenza-like syndrome, severe bronchiolitis with pneumonia, German measles, congenital rubella, Varicella, herpes zoster, hepatitis B, hepatitis C. Viral diseases treatable by the compounds of this disclosure also include chronic viral infections, including hepatitis B and hepatitis C, and an infection caused by a coronavirus, such as SARS, MERS, and SARS-CoV-2.

In certain aspects, a bacterial infectious disease can be caused by one or more bacteria including, but not limited to, bacteria selected from class *Bacilli*, such as *Staphylococcus* spp., *Streptococcus* spp., *Enterococcus* spp., *Bacillus* spp., *Listeria* spp.; bacteria selected from phylum Actinobacteria, including, but not limited to, *Propionibacterium* spp., *Corynebacterium* spp., *Nocardia* spp., *Actinobacteria* spp. (such as bacteria selected from family Mycobacteriaceae); bacteria selected from class *Clostridia*, including, but not limited to, *Clostridium* spp.; bacteria selected from phylum *Proteobacteria* (e.g., *Betaproteobacteria* and *Gammaproteobacteria*), including Enterobactericeae (e.g., *E. coli*, *Klebsiella pneumoniae*), Bacteroidetes (e.g., *Bacteroides fragilis*), Vibrionaceae (*Vibrio cholerae*), Pasteurellaceae (e.g., *Haemophilus influenzae*), Pseudomonadaceae (e.g., *Pseudomonas aeruginosa*), Neisseriaceae (e.g. *Neisseria meningitidis*), Rickettsiae, Moraxellaceae (e.g., *Moraxella catarrhalis*), any species of *Proteeae*, *Acinetobacter* spp., Helicobacter spp., and Campylobacter spp. Stenotrophomonas, Bdellovibrio, acetic acid bacteria, Legionella or alpha-proteobacteria such as Wolbachia; and bacteria selected from cyanobacteria, spirochaetes, green sulfur, or green non-sulfur bacteria. For example, the bacterium can be selected from S. aureus, including methicillin-resistant S. aureus, S. pneumoniae, S. pyogenes, H. influenza, M. catarrhalis, Legionella pneumophila, CoNS, S. pyogenes, S. agalactiae, E. faecalis, E. faecium, E. coli, Klebsiella pneumoniae, and M. tuberculosis. For example, an infectious disease is tuberculosis.

In certain aspects, the fungal infection is caused by one or more fungi including, but not limited to, fungi selected from the group consisting of Epidermophyton floccosum, Trichophyton rubrum, Trichophyton mentagrophytes, the Microsporum genera, the Trychophyton genera, Candida auris, Candida albicans, Candida lusitaniae, Candida kruseii, Candida glabrata, Candida parapsilosis, Candida tropicalis, Candida guilliermondii, Cryptococcus neoformans, Trichophyton tonsurans, Microsporum canis, Epidermophyton floccosum, Histoplasma capsulatum, blastomyces, Cryptoccus neoformans, Pneumocystis jiroveci, Cocidioides immitis, Aspergillus fumigatus, Aspergillus niger, Penicillium genera, and Cladosporium genera.

In a sixth embodiment, the present invention is a method of promoting wound healing in a patient in need thereof, comprising contacting a wound of the subject with a device of any one of the aspects of the first embodiment described above.

Promoting wound healing includes, but is not limited to, debridement, anti-infective prophylaxis, promotion of scar formation, and prevention of excessive scarification.

It is contemplated that the devices and methods of use described herein are applicable not only to open skin wounds, but also to wounds in muscle and other tissues, as well as for prophylaxis of infection or excessive scarification of any tissue surface. To accomplish these goals, the relative fraction of the dehydrated honey in the material delivered by microneedles, or from which the microneedles are made, can be varied in accordance with the intended use.

EXAMPLES

Example 1. Bacterial Killing Assay

For the bacterial killing assay, the vacuumed or cooked honey was prepared in disc shape and then the discs were dissolved into solutions. 10% and 1% honey solutions were incubated with methicillin-resistant S. aureus (MRSA) (supplied by the Division of Comparative Medicine, MIT) to assess for bacterial killing efficacy (FIG. 7). Briefly, MRSA was cultured in Trypsin Soy Broth (TSB) overnight to reach optimal growth phase. The MRSA broth was diluted with TSB until an O.D. of 0.76 in order to make the stock solution of the bacteria (~8×10$^8$ CFU/mL). Serial dilutions of the bacterial stock were made in various culture broth conditions: TSB (negative control), 1% vacuum, cooked, and raw honey, 10% vacuum, cooked, and raw honey, and 50% raw honey (positive control). Earlier experiments demonstrated that honey did not have a bactericidal effect when immediately plated and cultured, indicating that honey requires some co-incubation with the bacteria and kills in a time and concentration-dependent manner. For this set of experiments, 80 μL of each honey preparation was plated in a 96-well plate and incubated overnight at 37° C., and one aliquot was directly plated on blood agar and incubated overnight to verify culture purity. The following day, each honey preparation was plated onto a blood agar culture dish, using 10 μL in triplicate, incubated at 37° C. for 24 hours and then the plates were imaged and assessed for bacterial growth (FIG. 8). The experiments were run in triplicate. One of the raw honey preparations had a fungal contaminant, therefore only duplicate of this condition was evaluated.

Wound Healing Assay

Figure 11:
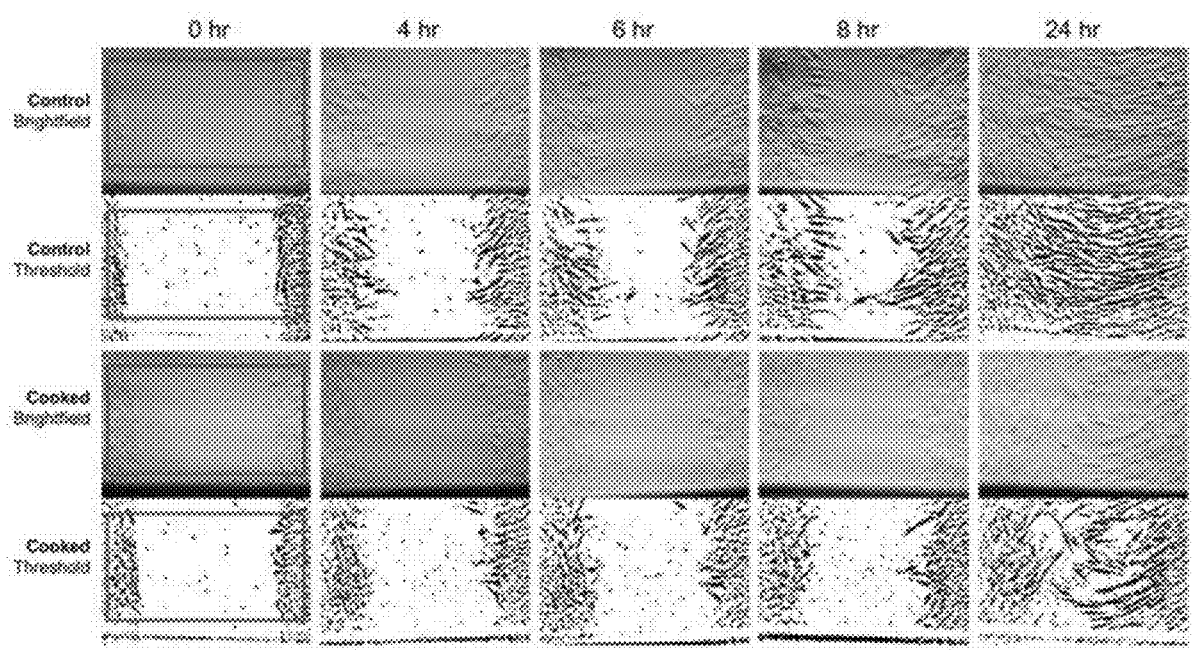
FIG. 11 shows wound-healing assay image analysis: representative bright field microscopy images (10×) of a single set of insert wound healing experiments. The top two rows show the negative control preparation and the bottom two rows is the cooked honey preparation. The second and fourth row are the corresponding thresholded images that were used for the image analysis, where the percent wound closure was calculated based on the change in black-to-white ratio in the image. Bottom black line in each image is the black marker used for orientation and image analysis. The red squares on the left are representative areas that were included in the image analysis. The black marker line area was not included so as to not skew the results.

For the wound healing assay, human dermal fibroblasts were cultured with 0.1% of raw, cooked, and vacuum-prepared honey solutions to assess their effect on wound closure. Two wound closure models were used: scratch and insert model. Briefly, normal human dermal fibroblasts (ATCC, PCS-201-012), were cultured overnight in fibroblast basal medium (ATCC, PCS-201-030) with low serum (ATCC, PCS-201-041). The media was removed, and trypsin was used to detach the cells from the culture flask. The cells were then centrifuged at 1200 rpm for 2 minutes and the supernatant was discarded. A cell suspension of 7×10$^5$ cells/mL was prepared. A black line was drawn on the bottom of a 12-well plate to allow for location identification during subsequent image analysis. For the insert assay, a 2-well insert (ibidi, Madison, WI) was placed on the bottom of the well. 70 μL of the suspension were added to each well, with the insert. The cells were incubated for 36 to 48 hours to become confluent, and then the 2-well insert was removed from the insert well. Picture were taken at this time for baseline (FIG. 11). For scratch assay, 2×10$^5$ cells/ml was prepared and 1 ml of cells per well was plated in 24 well plates and incubated for 36 to 48 hrs to become confluent. Then, a 200 μL pipette tip was used to create scratch. For both insert and scratch assay, the media is then removed from each well and washed twice with growth media to remove the detached cells. Then 1 mL of the growth media with 0.1% of raw, cooked, and vacuum-prepared honey was added. Pictures were taken at time 0, 4, 8, and 24 hours (6 hours for the insert condition). Each experiment was done in triplicate. For the image analysis, Image J was used to create thresholded, black and white images. These images were then used to calculate the percent of white and black space (representing the cell migration) in the images (FIG. 11).

Statistical Analysis

Statistical analysis and graphs of the various experiments presented in this study was performed using Microsoft Excel. Descriptive statistics performed included calculating of the means, standard deviation, standard error, percent change from baseline. These various parameters were then analyzed with a paired t-test with a p-value of 0.05 being considered significant.

While this invention has been particularly shown and described with references to example embodiments thereof, it will be understood by those skilled in the art that various changes in form and details may be made therein without departing from the scope of the invention encompassed by the appended claims.

The teachings of all patents, published applications and references cited herein are incorporated by reference in their entirety.

What is claimed is:

1. A device, comprising a base, and a plurality of microneedles attached to the base, wherein:
   the microneedles comprise dehydrated honey having water content of not greater than 1% by weight; and the honey is dehydrated by vacuum treatment.

2. The device of claim 1, wherein the base comprises dehydrated honey having water content of less than 1% by weight.

3. The device of claim 1, wherein the dehydrated honey has water content not greater than 0.5%.

4. The device of claim 1, wherein the microneedles further include a water-soluble polymer material, wherein the polymer material is mixed with the dehydrated honey.

5. The device of claim 1, wherein the microneedles include a scaffold material, wherein the scaffold material is coated with the dehydrated honey.

6. The device of claim 1, wherein the base is composed of the dehydrated honey.

7. The device of claim 1, wherein the device includes at least one additional active pharmaceutical ingredient (API).

8. The device of claim 7, wherein the additional API is selected from a phage, an antiviral agent, an antifungal agent, an anti-parasitic agent, an antibacterial agent, a chemotherapeutic agent, an antibody, a cytokine, a growth factor, hormone, a vaccine, a nucleic acid, a nucleic acid modifying agent, a nutraceutical agent, an anesthetic, a sedative, or a narcotic-blocking or narcotic-reversing agent.

9. The device of claim 7, wherein the additional API is a peptide or a protein.

10. The device of claim 1, further including a substrate layer disposed on the base.

11. The device of claim 1, wherein the dehydrated honey is a dehydrated Manuka honey.

\* \* \* \* \*